US006811341B2

(12) United States Patent
Crane

(10) Patent No.: US 6,811,341 B2
(45) Date of Patent: Nov. 2, 2004

(54) MULTIPLE-COMPONENT COMBINING

(75) Inventor: Richard Scott Crane, Hackettstown, NJ (US)

(73) Assignee: Closure Medical Corporation, Raleigh, NC (US)

( * ) Notice: Subject to any disclaimer, the term of this patent is extended or adjusted under 35 U.S.C. 154(b) by 187 days.

(21) Appl. No.: 10/211,124

(22) Filed: Aug. 2, 2002

(65) Prior Publication Data

US 2003/0040141 A1 Feb. 27, 2003

Related U.S. Application Data

(60) Provisional application No. 60/312,348, filed on Aug. 16, 2001.

(51) Int. Cl.[7] .............................. B67B 7/20; B67D 5/00
(52) U.S. Cl. ..................... 401/134; 222/83; 401/132; 604/3
(58) Field of Search ............................ 401/134, 133, 401/132; 222/83; 604/3

(56) References Cited

U.S. PATENT DOCUMENTS

| | | | |
|---|---|---|---|
| 1,332,985 A | | 3/1920 | Jarrett |
| 1,680,269 A | * | 8/1928 | Wellman et al. ......... 401/133 X |
| 1,962,875 A | | 6/1934 | Reber |
| 2,133,122 A | | 10/1938 | Swain .......................... 99/180 |
| 2,705,579 A | | 4/1955 | Mason ........................ 222/129 |
| 2,721,858 A | | 10/1955 | Joyner et al. |
| 3,254,111 A | | 5/1966 | Hawkins et al. |
| 3,450,129 A | | 6/1969 | Avery et al. |
| 3,481,676 A | * | 12/1969 | Schwartzman .............. 401/134 |
| 3,495,917 A | | 2/1970 | Truhan |
| 3,519,364 A | | 7/1970 | Truhan |
| 3,520,306 A | | 7/1970 | Gardner et al. ............. 128/335 |
| 3,524,537 A | | 8/1970 | Winter ......................... 206/47 |
| 3,559,652 A | | 2/1971 | Banitt et al. ................. 128/334 |

(List continued on next page.)

FOREIGN PATENT DOCUMENTS

| | | |
|---|---|---|
| GB | 2 107 328 A | 4/1983 |
| WO | WO 00/12411 | 2/2000 |
| WO | WO 00/38777 | 7/2000 |

OTHER PUBLICATIONS

U.S. patent application Ser. No. 08/266,647, Clark et al., filed Jun. 1994.

U.S. patent application Ser. No. 09/069,875, Narang, filed Apr. 1998.

U.S. patent application Ser. No. 09/069,979, Narang et al., filed Apr. 1998.

U.S. patent application Ser. No. 09/385,030, D'Alessio et al., filed Aug. 1999.

U.S. patent application Ser. No. 09/430,177, Narang et al., filed Oct. 1999.

U.S. patent application Ser. No. 09/430,289, D'Alessio et al., filed Oct. 1999.

*Primary Examiner*—Gene Mancene
*Assistant Examiner*—Kathleen J. Prunner
(74) *Attorney, Agent, or Firm*—Oliff & Berridge, PLC

(57) ABSTRACT

A device for use in combining components to form a compound and for applying the compound to a substrate includes a first housing having a first-housing receptacle with a proximal end, a plunger including a proximal end and a distal end, the distal end being disposed in the proximal end of the first-housing receptacle, at least one penetrable barrier sealing the receptacle, and a first component of the compound disposed in the first-housing receptacle, where one of the first housing and the plunger includes an applicator tip retaining a second component of the compound and being separated from the first component by the at least one penetrable barrier.

29 Claims, 15 Drawing Sheets

U.S. PATENT DOCUMENTS

| | | | |
|---|---|---|---|
| 3,573,069 A | 3/1971 | Keller et al. .................. 99/174 |
| 3,728,375 A | 4/1973 | Coover, Jr. et al. ...... 260/465.4 |
| 3,730,337 A | 5/1973 | White ...................... 206/47 B |
| 3,786,820 A | 1/1974 | Kopfer ...................... 132/74.5 |
| 3,789,820 A | 2/1974 | Douglas et al. ......... 123/27 GE |
| 3,802,604 A * | 4/1974 | Morane et al. ................ 222/83 |
| 3,835,834 A | 9/1974 | Brown et al. .............. 128/2 W |
| 3,940,362 A | 2/1976 | Overhults ................ 260/42.16 |
| 3,970,505 A | 7/1976 | Hauser et al. ............... 156/331 |
| 3,995,641 A | 12/1976 | Kronenthal et al. ........ 128/335 |
| 4,014,748 A | 3/1977 | Spinner et al. ............. 195/127 |
| 4,138,014 A | 2/1979 | Bouman .................... 206/542 |
| 4,206,843 A | 6/1980 | Rainey ...................... 206/216 |
| 4,211,323 A | 7/1980 | Olsen ........................ 206/210 |
| 4,297,160 A | 10/1981 | Kusayama et al. ...... 156/331.1 |
| 4,313,865 A | 2/1982 | Teramoto et al. .......... 260/31.4 |
| 4,340,708 A | 7/1982 | Gruber ...................... 526/313 |
| 4,364,876 A | 12/1982 | Kimura et al. ........... 260/465.4 |
| 4,430,013 A | 2/1984 | Kaufman ................... 401/132 |
| 4,560,723 A | 12/1985 | Millet et al. ................ 524/486 |
| 4,690,676 A | 9/1987 | Moulding, Jr. et al. ..... 604/189 |
| 4,707,450 A | 11/1987 | Nason ....................... 435/295 |
| 4,720,513 A | 1/1988 | Kameyama et al. ........ 523/203 |
| 4,747,719 A | 5/1988 | Parkin ....................... 401/132 |
| 4,777,230 A | 10/1988 | Kamath ....................... 526/86 |
| 4,781,696 A | 11/1988 | Moulding, Jr. et al. ..... 604/189 |
| 4,844,251 A | 7/1989 | Gueret ....................... 206/222 |
| 4,877,036 A | 10/1989 | Saint-Amand .............. 128/749 |
| 4,880,111 A | 11/1989 | Bagwell et al. .......... 206/209.1 |
| 4,903,708 A | 2/1990 | Saint-Amand .............. 128/749 |
| 4,930,637 A | 6/1990 | DeRoseau .................. 206/541 |
| 4,944,427 A | 7/1990 | Yamada et al. ............. 220/406 |
| 5,016,651 A | 5/1991 | Stalcup et al. .............. 128/898 |
| 5,038,938 A | 8/1991 | Berndt ....................... 206/571 |
| 5,042,690 A * | 8/1991 | O'Meara ...................... 222/83 |
| 5,066,299 A | 11/1991 | Bellingham ................ 606/213 |
| 5,130,369 A | 7/1992 | Hughes et al. .............. 524/846 |
| 5,167,973 A | 12/1992 | Snyder ....................... 426/115 |
| 5,203,459 A | 4/1993 | Wade ......................... 206/572 |
| 5,216,096 A | 6/1993 | Hattori et al. .............. 526/201 |
| 5,232,774 A | 8/1993 | Otsuka et al. ........... 428/321.5 |
| 5,259,835 A | 11/1993 | Clark et al. ................... 602/48 |
| 5,277,920 A | 1/1994 | Weaver, Jr. ................. 426/115 |
| 5,292,333 A | 3/1994 | Johnson ..................... 606/214 |
| 5,328,687 A | 7/1994 | Leung et al. ............. 424/78.35 |
| 5,456,361 A | 10/1995 | Walsh et al. ................ 206/570 |
| 5,490,736 A | 2/1996 | Haber et al. .................. 401/40 |
| 5,514,371 A | 5/1996 | Leung et al. ............. 424/78.35 |
| 5,514,372 A | 5/1996 | Leung et al. ............. 424/78.35 |
| 5,562,705 A | 10/1996 | Whiteford ................... 606/215 |
| 5,569,302 A | 10/1996 | Proto et al. ................. 606/228 |
| 5,582,834 A | 12/1996 | Leung et al. ............... 424/426 |
| 5,624,669 A | 4/1997 | Leung et al. ............. 424/78.35 |
| 5,636,931 A | 6/1997 | Gueret ....................... 401/126 |
| 5,660,273 A | 8/1997 | Discko, Jr. ................. 206/229 |
| 5,727,679 A | 3/1998 | Newarski .................... 206/222 |
| 5,757,997 A | 5/1998 | Birrell et al. ................. 385/60 |
| 5,769,552 A * | 6/1998 | Kelley et al. ............... 401/132 |
| 5,779,053 A | 7/1998 | Partika et al. .............. 206/570 |
| 5,782,568 A | 7/1998 | Roder et al. ................ 401/122 |
| 5,794,774 A | 8/1998 | Porcelli ...................... 206/369 |
| 5,803,638 A | 9/1998 | Gueret ....................... 401/122 |
| 5,928,611 A | 7/1999 | Leung ........................ 422/131 |
| 5,947,296 A | 9/1999 | Castora ...................... 206/571 |
| 5,979,658 A | 11/1999 | Allen et al. ................. 206/572 |
| 5,986,246 A | 11/1999 | Lee ............................ 219/723 |
| 5,989,205 A | 11/1999 | Pond et al. ..................... 604/3 |
| 6,010,462 A | 1/2000 | Stoermer, III ............... 600/572 |
| 6,012,586 A | 1/2000 | Misra ........................ 206/571 |
| 6,085,907 A | 7/2000 | Hochmeister et al. ...... 206/569 |
| 6,105,761 A | 8/2000 | Peuker et al. ............... 206/229 |
| 6,116,414 A | 9/2000 | Discko, Jr. ................. 206/229 |
| 6,143,805 A | 11/2000 | Hickey et al. .............. 522/152 |
| 6,183,593 B1 | 2/2001 | Narrang et al. ............. 156/327 |
| 6,186,971 B1 | 2/2001 | Naughton ...................... 604/2 |
| 6,193,108 B1 * | 2/2001 | Lepsius et al. ................ 222/83 |
| 6,206,192 B1 | 3/2001 | Winstead et al. ........... 206/572 |
| 6,213,767 B1 | 4/2001 | Dixon et al. ................... 433/9 |
| 6,216,885 B1 | 4/2001 | Guillaume ............... 211/85.13 |
| 6,217,603 B1 | 4/2001 | Clark et al. ................. 606/214 |
| 6,228,324 B1 | 5/2001 | Hasegawa et al. ............ 422/30 |
| 6,283,933 B1 | 9/2001 | D'Alessio et al. .............. 604/3 |
| 6,305,541 B1 | 10/2001 | Tanner et al. ............... 206/366 |
| 6,310,166 B1 | 10/2001 | Hickey et al. ........... 526/348.2 |
| 6,312,258 B1 | 11/2001 | Ashman ..................... 433/172 |
| 6,329,564 B1 | 12/2001 | Lebner ......................... 602/41 |
| 6,340,097 B1 | 1/2002 | D'Alessio et al. ......... 222/12.9 |
| 6,341,694 B1 | 1/2002 | Dawood ..................... 206/572 |
| 6,447,476 B1 | 9/2002 | Sogaro ......................... 604/85 |
| 6,455,064 B1 | 9/2002 | Narrang et al. ............. 424/447 |
| 6,512,023 B1 | 1/2003 | Malofsky et al. ........... 523/111 |
| 6,579,469 B1 | 6/2003 | Nicholson et al. ..... 252/182.11 |
| 2002/0066686 A1 | 6/2002 | Montenieri et al. ......... 206/365 |

* cited by examiner

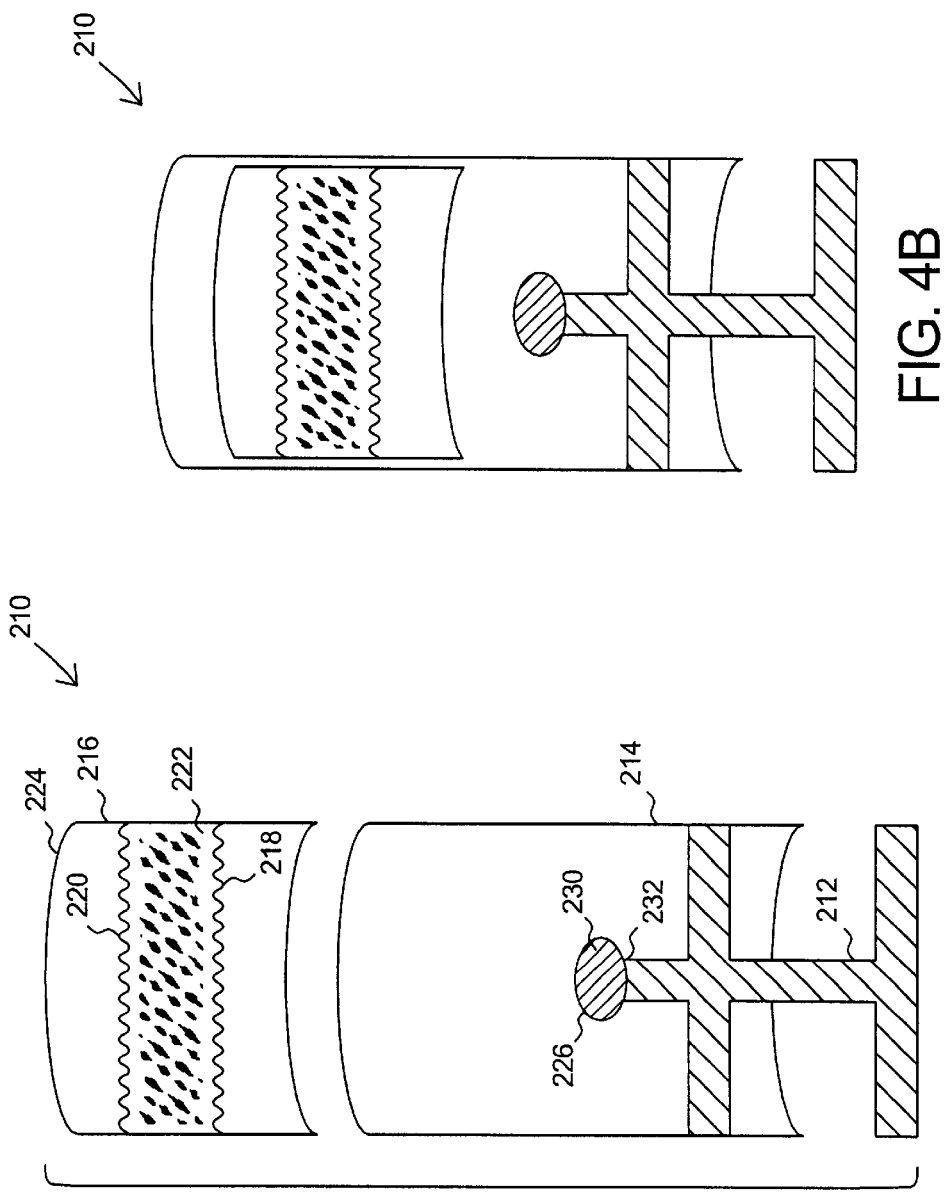

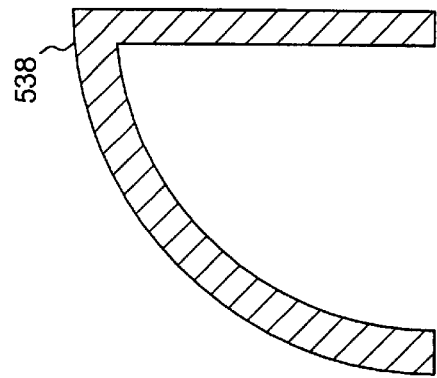
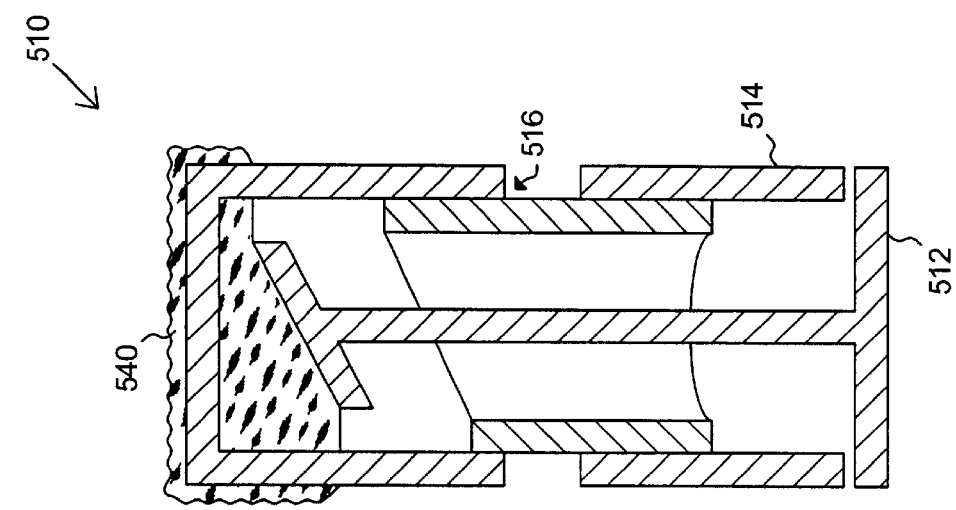
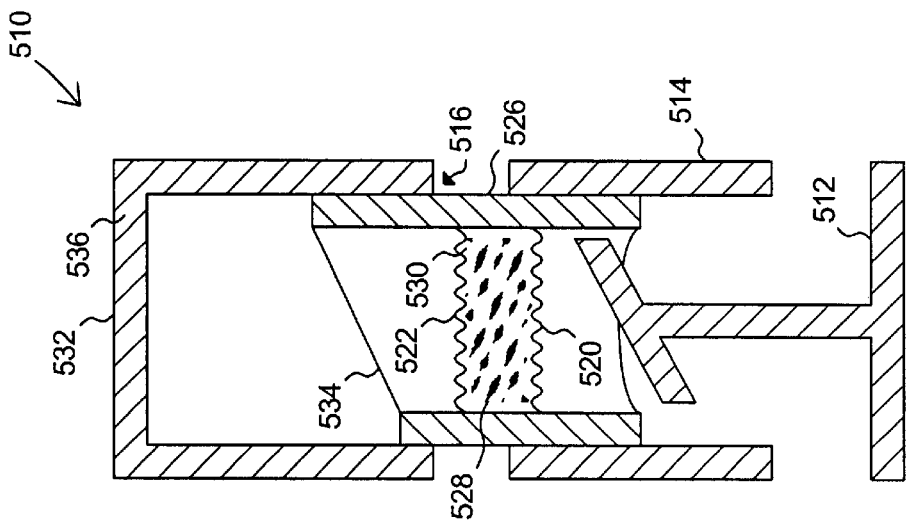
FIG. 6C
FIG. 6B
FIG. 6A

MULTIPLE-COMPONENT COMBINING

CROSS-REFERENCE TO RELATED ACTIONS

This application claims the benefit of U.S. Provisional Application No. 60/312,348 filed Aug. 16, 2001.

FIELD OF THE INVENTION

The invention relates to material applicators and more particularly applicators for mixing and applying multiple components to a substrate.

BACKGROUND OF THE INVENTION

Often, multiple components may be mixed to form desirable compounds. For example, epoxies may be formed by mixing components of the epoxies, and are desirable for bonding items, e.g., broken items. Additionally, polymerizable and/or cross-linkable materials may be combined with polymerization or cross-linking initiators (catalysts) to form desirable compounds, e.g., for adhering items such as wounds. It is typically desirable to keep the components to be mixed separate until it is desired to use the compound, e.g., to prevent the compound from being formed and curing such that it is unusable when then time comes to use it.

SUMMARY OF THE INVENTION

In general, in an aspect, the invention provides a device for use in combining components to form a compound and for applying the compound to a substrate. The device includes a first housing having a first-housing receptacle with a proximal end, a plunger including a proximal end and a distal end, the distal end being disposed in the proximal end of the first-housing receptacle, at least one penetrable barrier sealing the receptacle, and a first component of the compound disposed in the first-housing receptacle, where one of the first housing and the plunger includes an applicator tip retaining a second component of the compound and being separated from the first component by the at least one penetrable barrier.

Implementations of the invention may include one or of the following features. The device further includes a second housing, that provides a second-housing receptacle, and a cartridge comprising a cartridge housing that provides a cartridge-housing receptacle and that is configured to be securely and releasably received by the first-housing receptacle. The the at least one penetrable barrier includes at least two penetrable barriers sealing the cartridge-housing receptacle and wherein the first component is disposed between the at least two penetrable barriers. The at least one penetrable barrier includes at least two penetrable barriers sealing the first-housing receptacle and wherein the first component is disposed between the at least two penetrable barriers. The applicator tip is coupled to the first housing at a distal end of, and in fluid communication with, the first-housing receptacle.

Implementations of the invention may also include one or more of the following features. The applicator tip is coupled to the distal end of the plunger, and wherein the first housing includes a back wall providing a closed distal end of the first-housing receptacle, and wherein the at least one penetrable barrier is disposed between the back wall and the distal end of the plunger. The first component of the compound is disposed in the receptacle between a distal end of the receptacle and the at least one penetrable barrier. A distal end of the plunger is configured to at least one of facilitate penetration of the at least one penetrable barrier by the distal end of the plunger, and direct the first compound in a desired direction.

In general, in another aspect, the invention provides a device for use in combining components of a compound for application to a substrate. The device includes a body providing a body cavity, a first penetrable membrane sealing the body cavity, a second penetrable membrane sealing the body cavity and being disposed distally in the body cavity relative to the first penetrable membrane, a first compound component disposed between the first and second penetrable membranes, and a second compound component disposed in the body cavity distally from the second penetrable membrane.

Implementations of the invention may include one or more of the following features. The body comprises a base, that provides a base cavity, and a cartridge comprising a cartridge housing that provides a cartridge-housing cavity and that is configured to be securely and removably received by the base cavity, the base cavity and the cartridge-housing cavity providing the body cavity while the cartridge housing is received by the base cavity. The first and second membranes and the first and second compound components are disposed within the cartridge-housing cavity. The body includes a porous tip disposed and covering a distal end of the body cavity. The tip includes a third compound component.

Implementations of the invention may also include one or more of the following features. The device further includes a plunger having a distal end configured to be extendable into the body cavity and to penetrate the first and second membranes. The plunger includes a tip configured to receive the first and second components. The device further includes a third penetrable membrane sealing the body cavity and disposed distally from the second penetrable membrane, wherein the second compound component is disposed between the second and third penetrable membranes. The device further including a fourth penetrable membrane sealing the body cavity and disposed distally from the first penetrable membrane and proximally from the second penetrable membrane, wherein the first compound component is disposed between the first and fourth penetrable membranes.

In general, in another aspect, the invention provides an apparatus for use in combining compound components to form a compound, and for use in applying the compound to a substrate, the apparatus including a plurality of containers each having an open, proximal end and a closed, distal end, at least one first penetrable membrane sealing the open, proximal end of each of the plurality of containers, a second penetrable membrane sealing a particular one of the containers between the corresponding open, proximal end and the corresponding closed, distal end, a first compound component disposed in the particular one of the containers between the first penetrable membrane and the second penetrable membrane, and a second compound component disposed in the particular one of the containers between the second penetrable membrane and the corresponding closed, distal end.

In general, in another aspect, the invention provides an apparatus for use in combining compound components to form a compound, and for use in applying the compound to a substrate, the apparatus including a plurality of first containers each having a first open, proximal end and a first closed, distal end, a plurality of second containers each coupled and corresponding to a respective first container, each of the second containers having a second open, proximal end and a second closed, distal end, at least one penetrable membrane sealing the first open, proximal ends of the plurality of first containers, at least one cover disposed over the first open, proximal ends of the plurality of second containers, a plurality of devices disposed in the plurality of second containers and configured to hold the compound for application to the substrate, a first compound component disposed in at least a particular one of the first containers between the at least one penetrable membrane and the first closed, distal end of the particular first container, and a second compound component disposed in at least one of the at least a particular one of the first containers and at least one of the second containers.

Implementations of the invention may include one or more of the following features. At least a particular one of the devices disposed in the second containers has a tip having the second component. The at least a particular one of the devices is disposed adjacent to the at least a particular one of the first containers.

In general, in another aspect, the invention provides a cartridge for use with a housing that provides a receptacle, the cartridge including a body configured to be removably and securely received by the housing receptacle, the body providing a cavity extending from a proximal exterior surface of the body, a first penetrable barrier sealing the cavity, and a first compound component disposed distally in the cavity from the penetrable barrier.

Implementations of the invention may include one or more of the following features. The cartridge further includes a second penetrable barrier sealing the cavity and being displaced distally from the first penetrable barrier, and wherein the compound component is disposed between the first and second barriers. The cartridge further includes a third penetrable barrier sealing the cavity and being displaced distally from the second penetrable barrier, and a second compound component disposed in the cavity between the second and third compound components. The cartridge further includes a fourth penetrable membrane sealing the cavity and disposed distally from the second barrier and proximally from the third barrier, wherein the second compound component is disposed between the third and fourth compound components. The body comprises a substantially impenetrable wall covering a distal end of the cavity.

Implementations of the invention may also include one or more of the following features. The cartridge further includes a tip coupled to the body and covering a distal end of the cavity, the tip being configured to receive the first compound component. The tip includes a second compound component, and is configured to retain the compound, formed by the first and second compound components when the tip receives the first compound component, for application to a substrate.

In general, in another aspect, the invention provides a device for use in combining components to form a compound and for use in applying the compound to a substrate, the device includes a housing providing a receptacle at least partially through the housing and a hole through a wall of receptacle, a plunger including a proximal end and a distal end, at least the distal end being configured to be extendable into a proximal end of the receptacle in the housing, a penetrable barrier sealing the receptacle proximally relative to the hole provided by the housing, a frangible membrane sealing the hole provided by the housing, a first component of a compound disposed in the receptacle distally from the penetrable barrier, and a porous member coupled to the housing and disposed over the hole and the frangible membrane, the porous member retaining a second component of the compound and configured to receive the first component of the compound.

Various aspects of the invention may provide one or more of the following advantages. Compounds can be formed and applied easily. Applicators for combining and applying multiple components to a substrate can be used repeatedly, and/or can be single-use applicators. Applicators for combining and applying multiple components to a substrate can be adapted to be single- or multi-use depending upon the application. Applicator designs are adaptable to a broad range of materials and manufacturing processes.

These and other advantages of the invention, along with the invention itself, will be more fully understood after a review of the following figures, detailed description, and claims.

BRIEF DESCRIPTION OF THE FIGURES

FIGS. 4A–4C are cross-sectional views of another applicator in three different positions during assembly and use.

FIGS. 6A and 6B are cross-sectional views of another applicator in two different positions during use.

FIG. 6C is a cross-sectional view of an exemplary alternative configuration of a tip of the applicator shown in FIGS. 6A and 6B.

DETAILED DESCRIPTION OF PREFERRED EMBODIMENTS

At least some embodiments of the invention provide techniques for mixing and applying multiple components that form a compound when mixed. Exemplary applicators are configured to be easily reused, for example by including replaceable cartridges of compound components. Exemplary embodiments of the invention help keep compound components separate until mixing is desired, and to facilitate mixing and application of the formed compound to substrates. Other embodiments are within the scope of the invention.

Figure 1A:
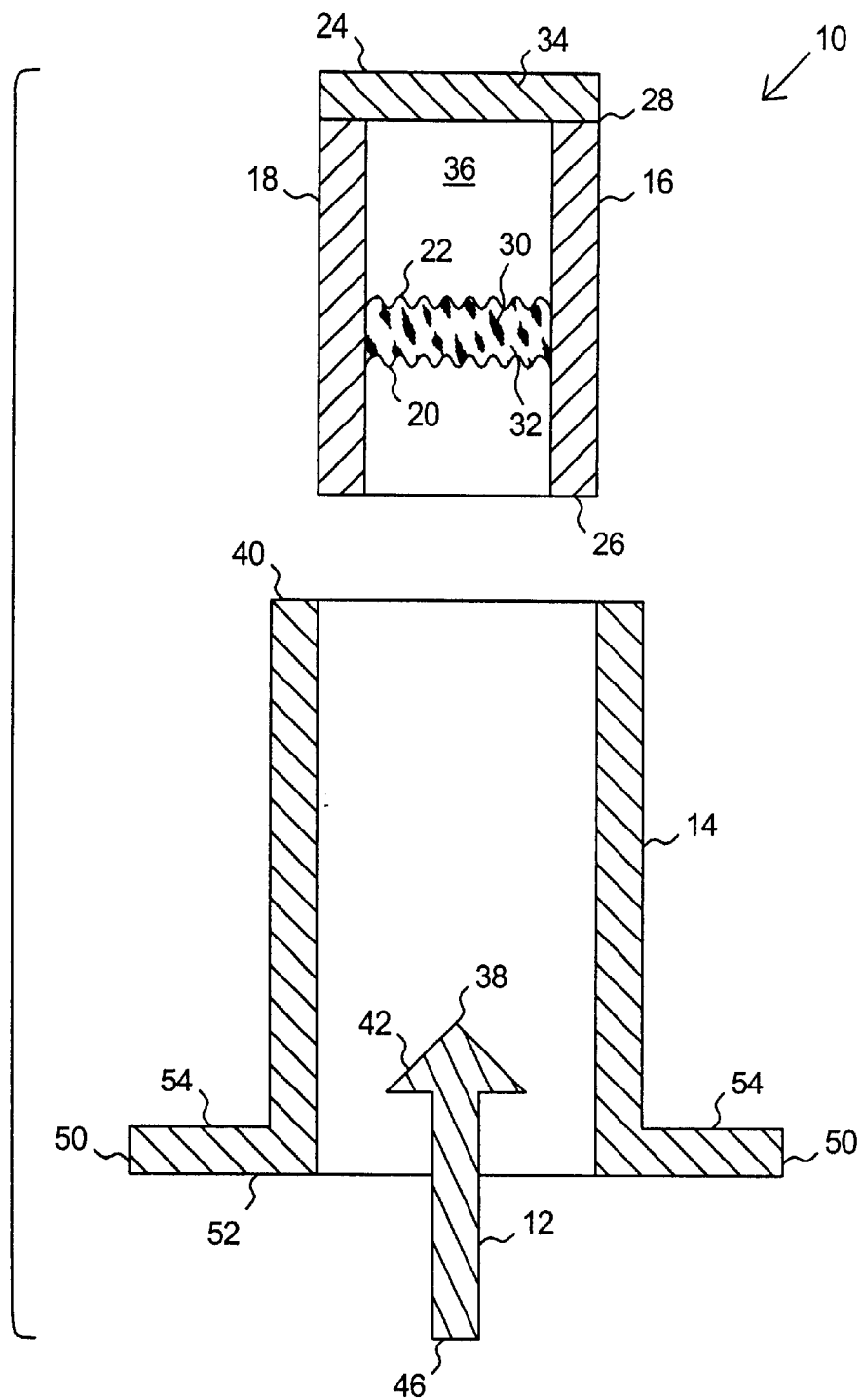
FIGS. 1A–1C are cross-sectional views of an applicator, for mixing and applying compound components, in three different positions during assembly and use.
Figure 1B:
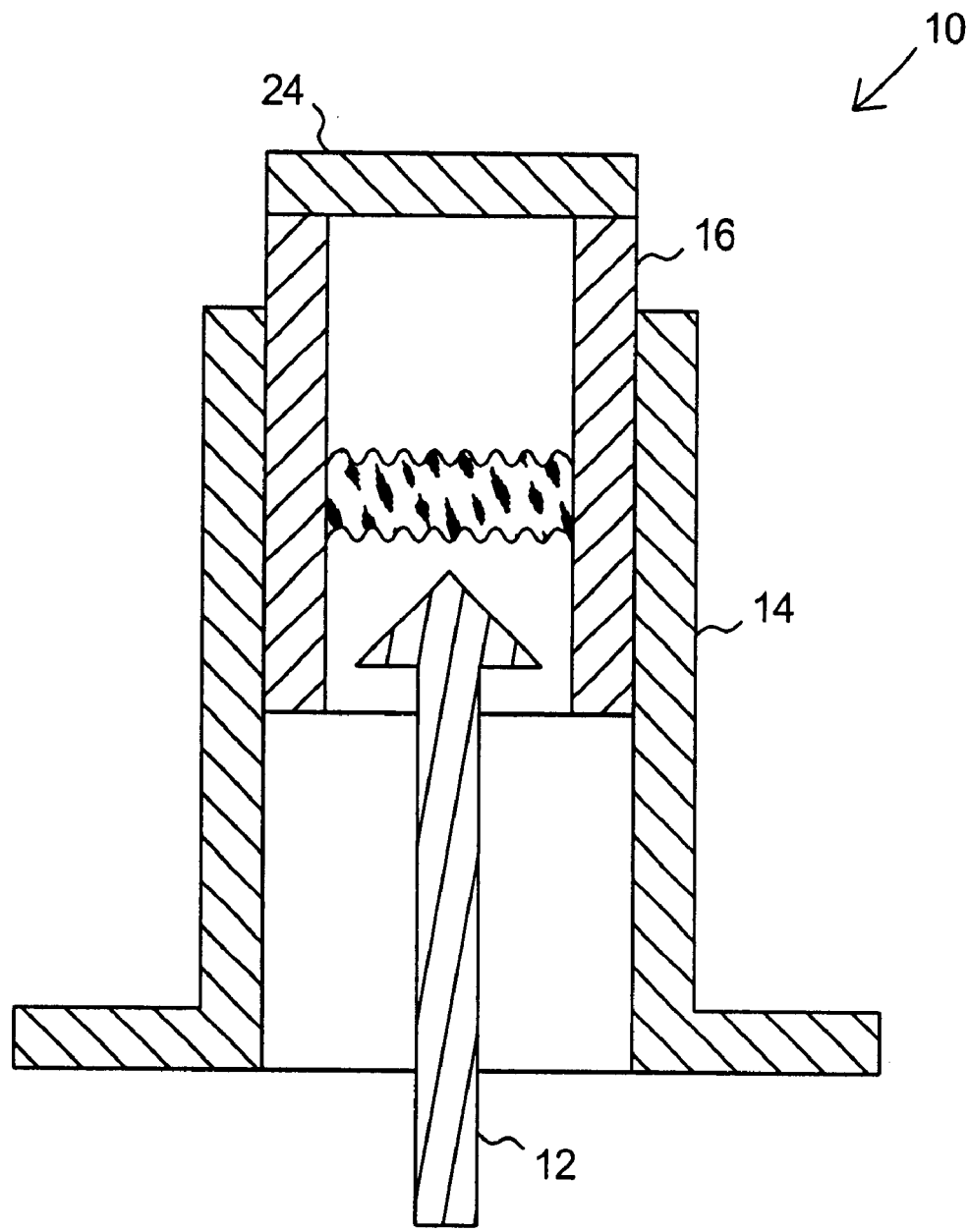
Figure 1C:
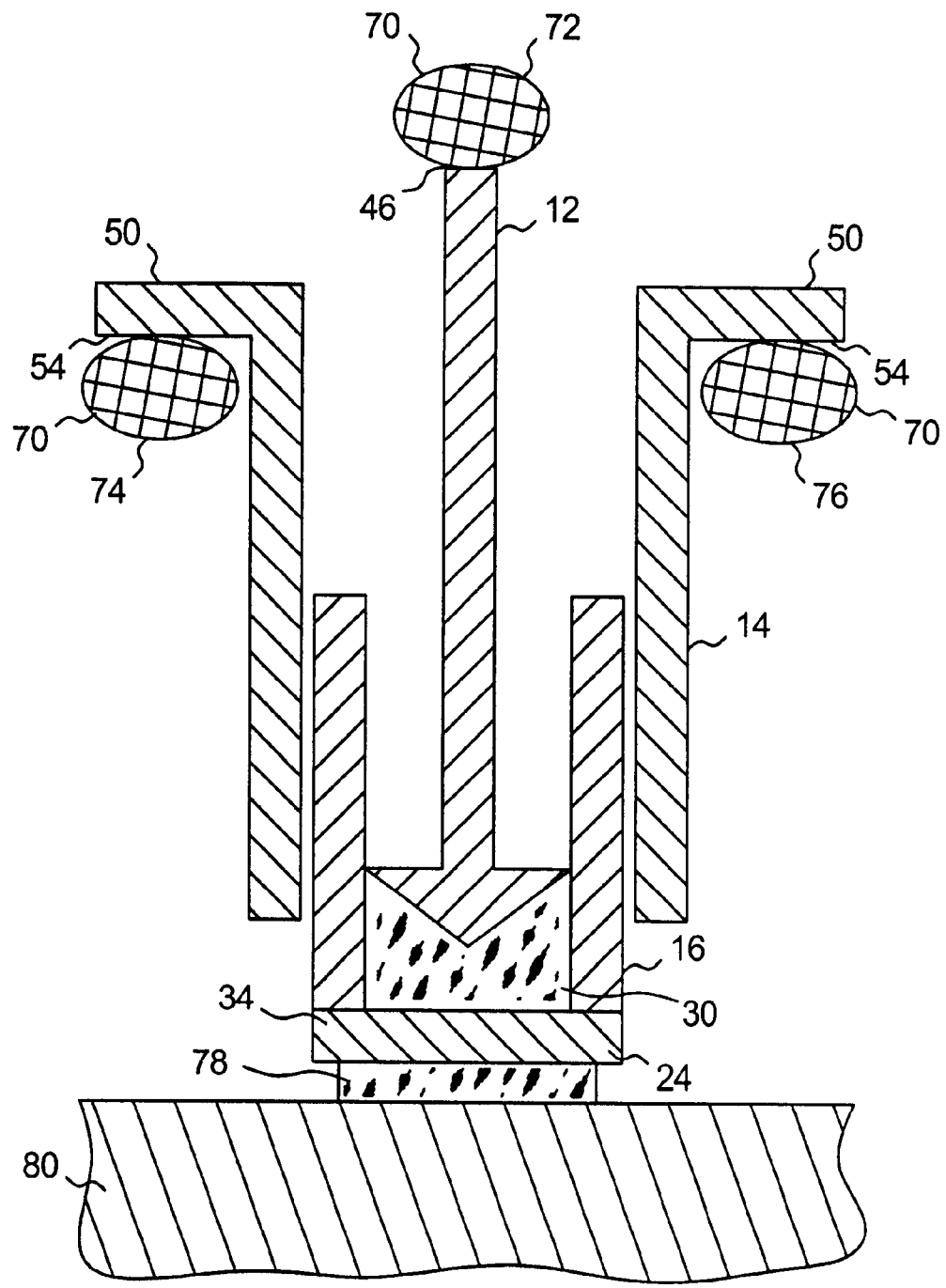

Referring to FIGS. 1A–1C, a compound applicator 10 includes a plunger 12, a tube 14, and a cartridge 16. The applicator 10 is configured to separately contain compound components and to allow mixing of the components when desired. The applicator 10 is further configured to facilitate application of the compound to a substrate including, but not limited to, human tissue. For human tissue applications, the applicator 10 is preferably made with surgical-grade materials. The applicator 10 is preferably configured to be reusable but may, however, be configured as a disposable, one-time use device.

The cartridge 16 is configured to contain components of a compound for mixing, while keeping the components separate until mixing is desired. The cartridge 16 includes a cylindrical cartridge tube 18, a proximal penetrable barrier 20, a distal penetrable barrier 22, and a porous tip 24. The tube 18 is sealed, preferably at or near a proximal end 26, by the barrier 20 and is sealed, preferably at or near a distal end 28, but displaced from the tip 24, by the barrier 22. Seals provided by the barriers 20, 22 form a chamber 32 with the tube 18 for holding a polymerizable and/or cross-linkable (PCL) material 30. The barrier 20 may be displaced inwardly (distally) from the proximal end 26 and the barrier 22 is preferably displaced inwardly (proximally) from the distal end 28. These barriers 20, 22 are made of a thin material that may be metallic and/or non-metallic. The barrier material is substantially or completely impermeable to the material 30 until penetrated. The barrier material and the seals are configured to inhibit the material 30 from passing to portions of the cartridge 16 outside the chamber 32, e.g., to contact the tip 24, until the barriers 20, 22 are penetrated. The tip 24 is disposed in fluid communication with the barrier 22 to receive the material 30 if the barrier 22 is penetrated.

The polymerizable and/or cross-linkable material 30 may be any of several materials. For example, the material 30 may be/include an alpha-cyanoacrylate, a higher cyanoacrylate analog, other modified alpha-cyanoacrylates, mixtures including alpha-cyanoacrylates, mixtures including viscosity modifiers, etc. Further exemplary materials are provided in U.S. Pat. No. 5,328,687, U.S. Pat. No. 5,928,611, U.S. Pat. No. 6,217,603, U.S. Pat. No. 3,728,375, U.S. Pat. No. 3,970,505, U.S. Pat. No. 4,297,160, U.S. Pat. No. 4,340,708, U.S. Pat. No. 4,777,230, U.S. Pat. No. 5,130,369, and U.S. application Ser. No. 08/226,647.

The tip 24 contains a catalyst 34 and is configured to receive the material 30 and to facilitate application of the compound formed by the material 30 and the catalyst 34 to a substrate. The tip 24 is preferably porous, being configured to hold the catalyst 34 and to receive the material 30 to form the compound, and to permit the compound to flow through the tip 24 for application to the substrate. The tip 24 is configured as a disc-shaped cap as shown in FIGS. 1A–1C, although other tip shapes are acceptable (e.g., see FIGS. 5A–5C). Preferably, the tip 24 is configured to inhibit insertion of the tip 24 into the applicator tube 14 (e.g., by having a larger cross-section than the interior of the tube 14). Further examples of acceptable tips are provided in U.S. Pat. No. 5,928,611 and U.S. Pat. No. 6,217,603.

An empty region 36 is defined between the tip 24, the tube 18, and the distal barrier 22, providing fluid communication between the tip 24 and the barrier 22. The empty region 36 is large enough to enable a pointed or sharp end 38 of the plunger 12 to rupture or penetrate the distal barrier 22.

The cartridge tube 18 and the applicator tube 14 are configured for the applicator tube 14 to snugly receive the cartridge tube 18. The cartridge 16 is configured to be inserted into a distal end 40 of the applicator tube 14. The tube 14 is configured in conjunction with the cartridge tube 18 to hold the tube 18 in place during use (to mix the materials 30, 34 to form the compound and expel the compound through the tip 24) and to permit easy removal of the cartridge 16 from the tube 14, e.g., after use. For example, the applicator tube 14 and the cartridge tube 18 can be configured for secure, but releasable, attachment with a twist-lock feature, one or more mating tabs and/or recesses, or to be friction fit, or screwed together, or configured with similar mechanisms for secure, releasable mating.

The cartridge tube 18 is further configured to facilitate pushing of the plunger 12 into the tube 18. The tube 18 includes flanges 50 disposed at a proximal end 52 of the tube 18. The flanges 50 are configured to receive portions of a user's fingers on distal surfaces 54 similar to typical configurations of syringes. The flanges 50 may be a single flange that traverses a perimeter of the tube 18. The flanges 50 may be arched to receive the user's fingers.

The plunger 12 is configured to have its distal end 42 fit within the tube 14 and the cartridge tube 18. The distal end 42 is terminated with the sharp end or tip 38 that is configured to penetrate and rupture the penetrable barriers 20, 22 containing the material 30. The distal end 42 is also configured to push the material 30 contained by the barriers 20, 22 toward the tip 24 as the end 42 moves toward the distal end 28 of the cartridge tube 18. A proximal end 46 of the plunger 12 is configured to be pushed, e.g., by a thumb of a user (similar to a syringe plunger). Although the plunger 12 does not, the proximal end 46 may include a flange (see FIG. 3B).

The applicator 10 may be provided to a user in assembled, disassembled, or partially assembled form. Preferably, the applicator comes in partially-assembled form, with the distal end 42 of the plunger 12 being disposed in the tube 14 and the proximal end of the plunger 12 being disposed externally to the tube 14, and with the cartridge 16 being displaced from the tube 14. In this configuration, the user can assemble the applicator 10 by inserting the proximal end 26 of the cartridge 16 into the distal end 40 of the applicator tube 14. The user can insert the cartridge 16 until the tip 24 is disposed adjacent to the distal end 40. The applicator 10 may be provided fully assembled, especially if the applicator 10 is configured to be a single-use device.

Figure 2:
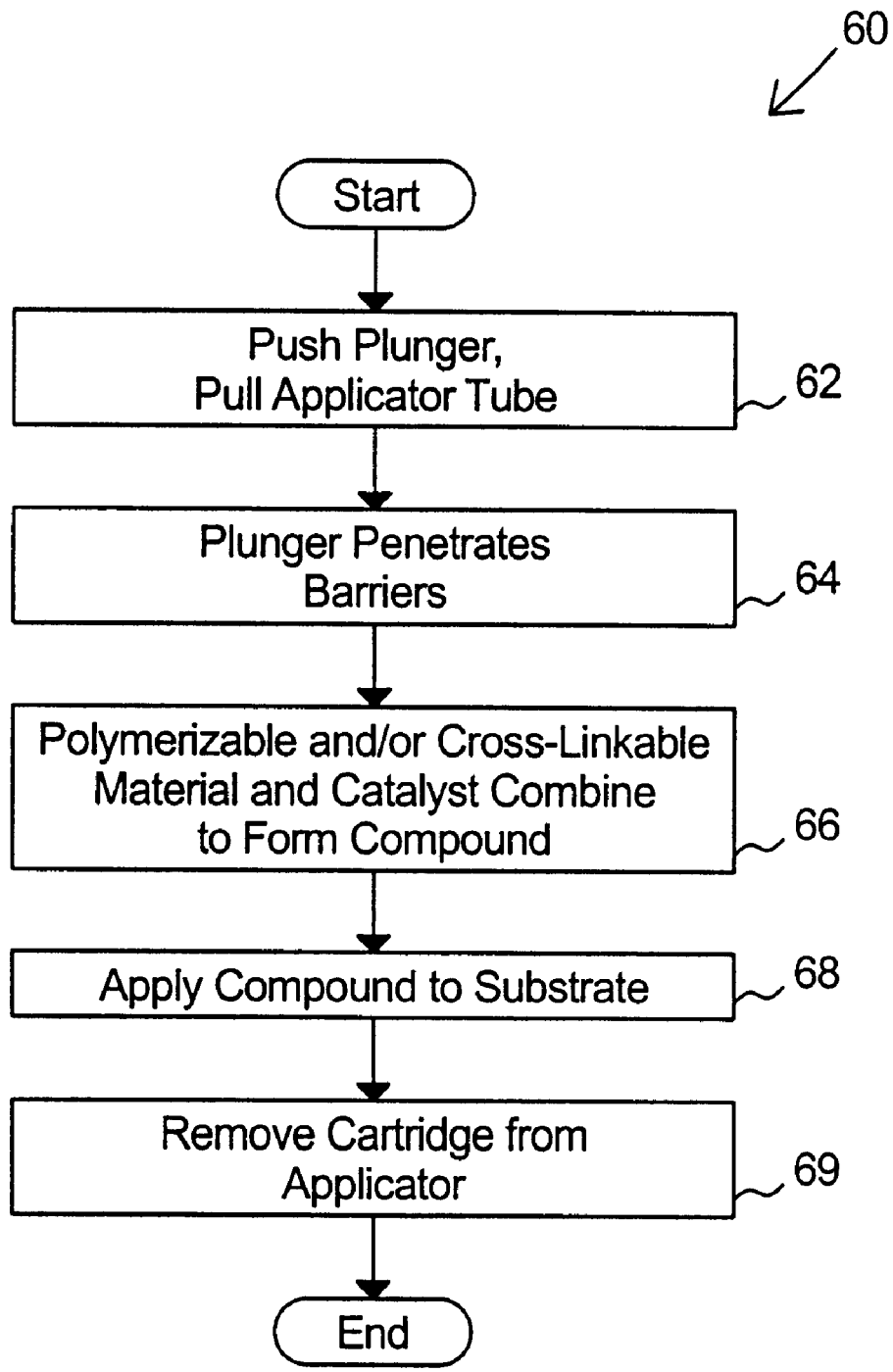
FIG. 2 is a block flow diagram of using the applicator shown in FIGS. 1A–1C.

In operation, referring to FIG. 2, with further reference to FIGS. 1B–1C, a process 60 for mixing the materials 30, 34 to form the compound and applying the compound using the applicator 10 includes the stages shown. The process 60, however, is exemplary only and not limiting. The process 60 can be altered, e.g., by having stages added, removed, or rearranged.

At stage 62, a user 70 pushes on (depresses) the plunger 12 while pulling on the applicator tube 14. As shown in FIG. 1C, the user's thumb 72 contacts and pushes on the proximal end 46 of the plunger 12 and the user's fingers 74, 76 (e.g., index and middle fingers) pull on the distal surfaces 54 of the flanges 50. This forces the plunger 12 distally relative to the applicator tube 14 and the cartridge 16.

At stage 64, the plunger 12 penetrates the barriers 20, 22 and pushes the polymerizable and/or cross-linkable material 30 into contact with the tip 24. The sharp end 38 of the plunger 12 ruptures the barriers 20, 22 and the distal end 42 of the plunger forces the material 30 into the tip 24.

At stage 66, the material 30 combines (e.g., mixes) with the catalyst 34 to form the compound 78. The material 30 is absorbed and/or adsorbed by the catalyst 34, with the catalyst 34 causing the material 30 to polymerize and/or cross-link to form the compound 78.

At stage 68, the user 70 applies the compound 78 to a substrate 80. The user 70 moves the applicator 10 into close proximity and/or contact with the substrate 80 such that the compound 78 contacts the substrate 80. For example, the compound 78 may be a surgical adhesive and the substrate 80 may be a portion of a person's body, e.g., a wound to be closed and/or protected.

At stage 69, the user 70 removes the cartridge 16. The user 70 pulls the cartridge 16 from the applicator tube 14, preparing the tube 14 for receipt of another cartridge 16 and re-performance of the process 60.

Other embodiments are within the scope and spirit of the invention and the appended claims.

Figure 3A:
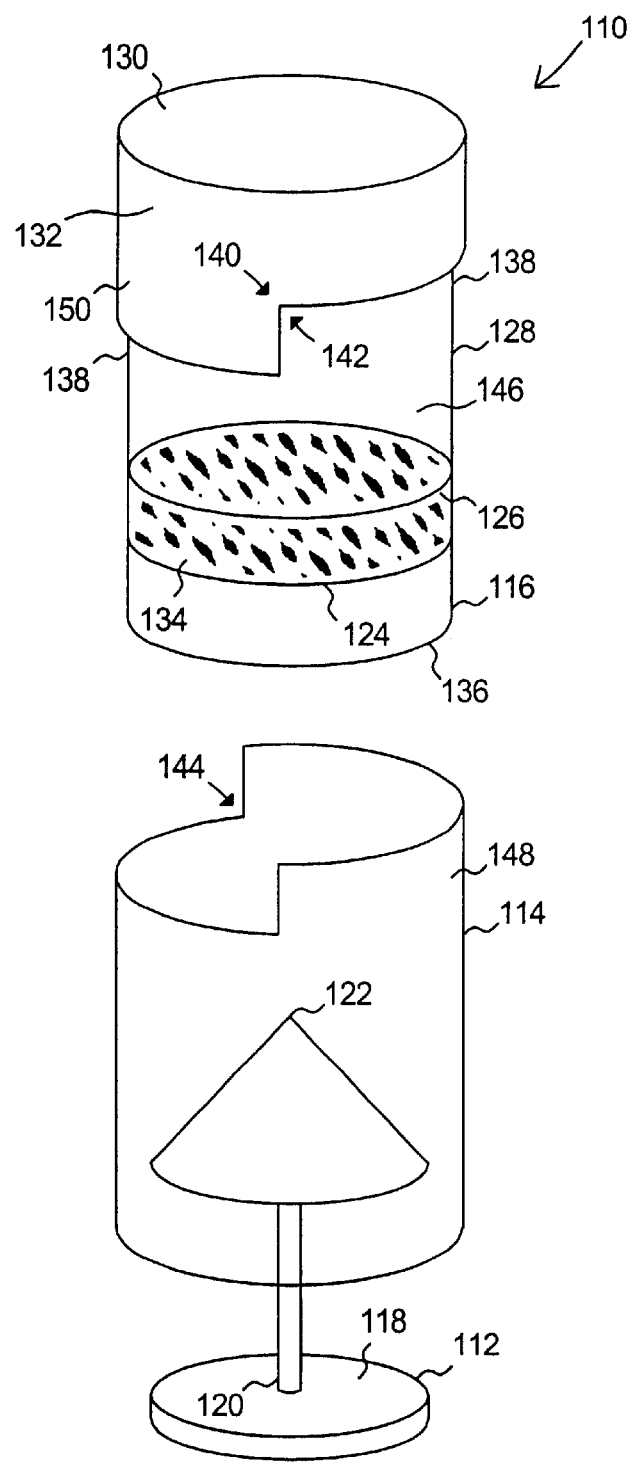
FIG. 3A is an exploded perspective view of another applicator.

Referring to FIG. 3A, another applicator 110 includes a plunger 112, an applicator tube 114, and a cartridge 116. The applicator 110 is configured for similar uses as the applicator 10 shown in FIG. 1A.

The plunger 112 is configured similarly to the plunger 12 shown in FIG. 1A. The plunger 112 is configured to fit within the tube 114 and the cartridge 116 and includes a flange 118, at a proximal end 120, for receiving a finger to push the plunger 112 into the tube 114 and the cartridge 116, and a pointed sharp tip 122. The tip 122 is configured to puncture penetrable barriers 124, 126 of the cartridge 116.

The cartridge 116 includes the penetrable barriers 124, 126, a cartridge tube 128, and a tip 130. The tip 130 is made of similar material as the tip 24 of the applicator 10 shown in FIG. 1A for receiving and holding a catalyst 132. The penetrable barriers 124, 126 seal the tube 128 and releasably retain a PCL material 134 in the tube 128. The barriers 124, 126 are disposed near a proximal end 136 and a distal end 138, respectively, of the tube 128. The barriers 124, 126 may be disposed at, or inwardly from, the ends 136, 138. The barrier 126 is displaced from the tip 130 sufficiently to allow the tip 122 of the plunger 112 to rupture the barrier 126 when the plunger 112 is pushed distally in the cartridge 116 toward the tip 130.

The tip 130 and the tube 128 are configured with corresponding, mating steps 140, 142, respectively. The step 140 of the tip 130 also corresponds and mates with a step 144 of the applicator tube 114. The step 142 of the tube 128 includes an extending wall 146 that is substantially semi-circular.

Figure 3B:
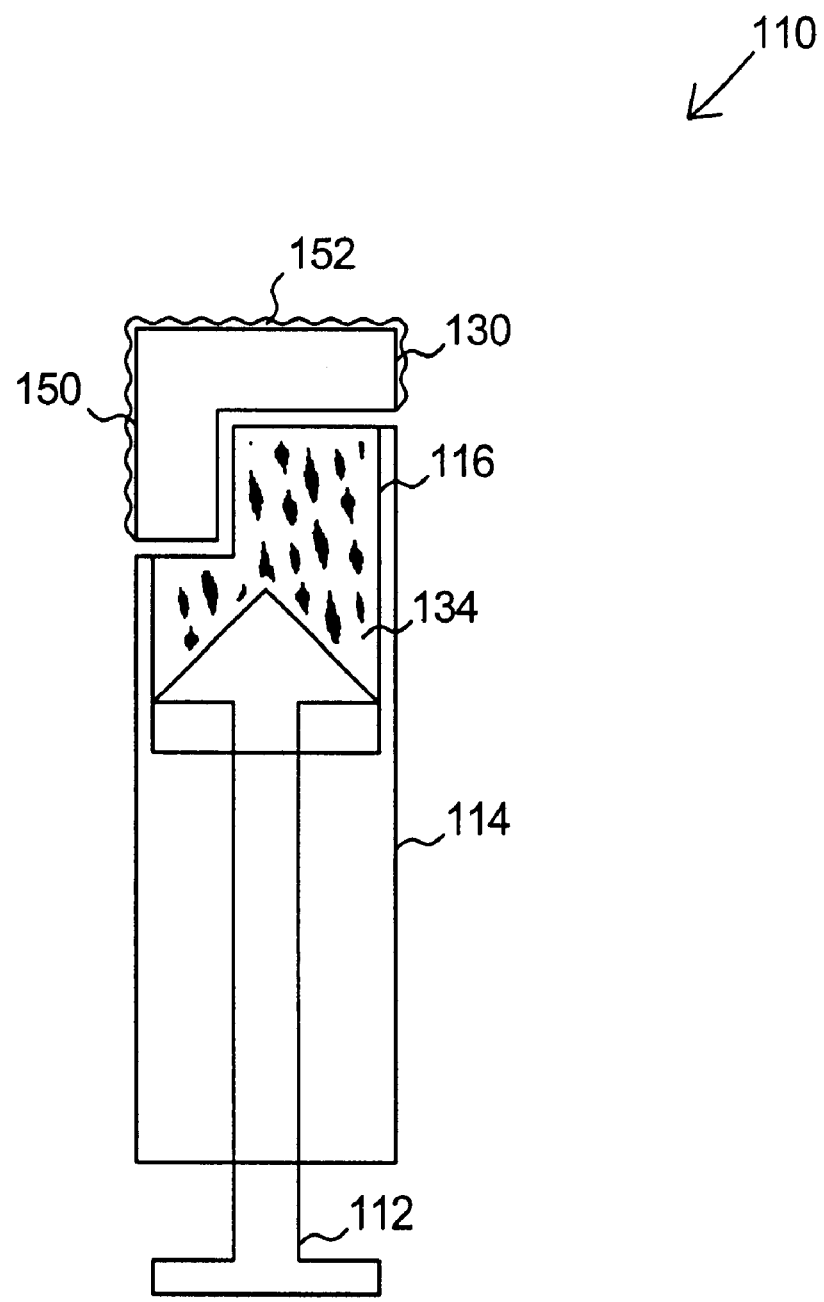
FIG. 3B is a cross-sectional view of the applicator shown in FIG. 3A.

Referring also to FIG. 3B, the applicator 110 can be assembled and used in manners similar to those for assembling and using the applicator 10. To assemble the applicator 110, the cartridge 116 is inserted into the applicator tube 114 such that the extending wall 146 of the cartridge tube 128 contacts a mating wall 148 of the applicator tube to hold the cartridge 116 in place. The cartridge 116 is preferably inserted into the tube 114 such that the step 142 of the tip 130 is disposed adjacent to the step 144 of the applicator tube 114 such that the tip 130, and in particular a side 150 of the tip 130, is exposed and available for delivering compound to a substrate. To use the applicator 110, the plunger 112 is pushed distally into the applicator tube 114 and the cartridge 116 such that the penetrable barriers 124, 126 are penetrated. The plunger 112 pushes the material 134 into the tip 130 such that the material 134 and the catalyst 132 combine to form a compound 152. The compound 152 may be applied to a substrate by moving the tip 130 into close proximity and/or contact with the substrate. The used cartridge 116 may be removed and replaced by a fresh/new cartridge 116.

Figure 4D:
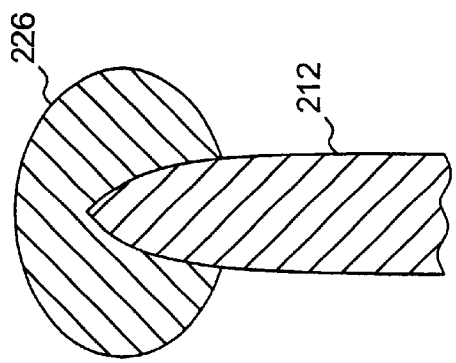
FIG. 4D is a cross-sectional view of a portion of a plunger of the applicator shown in FIGS. 4A–4C.

Referring to FIG. 4A, another applicator 210 includes a plunger 212, an applicator tube 214, and a cartridge 216. The applicator 210 is configured for similar uses as the applicators 10 shown in FIG. 1A and 110 shown in FIG. 3A.

The tube 214 and cartridge 216 are configured to have the cartridge securely inserted into the tube 214 via the proximal end of the tube 214. The cartridge 216 includes two penetrable barriers 218, 220 that seal the cartridge 216 and in conjunction with the cartridge 216 retain a PCL material 222. A top wall 224 of the cartridge 216 is also configured to be penetrable by a tip 226 of the plunger 212. The cartridge 216 alternatively may not have the top wall 224.

The plunger 212 is a swab-type plunger and includes a shaft 228, the tip 226, and flanges 234. The tip 226 is disposed on a distal end 232 of the shaft 228 and is configured to receive and retain a catalyst 230 and to penetrate the barriers 218, 220 and the top wall 224 of the cartridge 216. The shaft 228 may be configured to assist the plunger 212 to penetrate the barriers 218, 220 and the wall 224. For example, the distal end 232 can be pointed (see FIG. 4D) or otherwise sharp and the tip 226 configured to permit the distal end 232 to directly contact the barriers 218, 220 and the wall 224 (e.g., by moving aside upon contact with the barriers 218, 220 and the wall 224 and returning to its original shape upon separation from/penetration through the wall 224). The flanges 234 help guide the plunger 212 within the tube 214 and the cartridge 216.

Figure 4C:
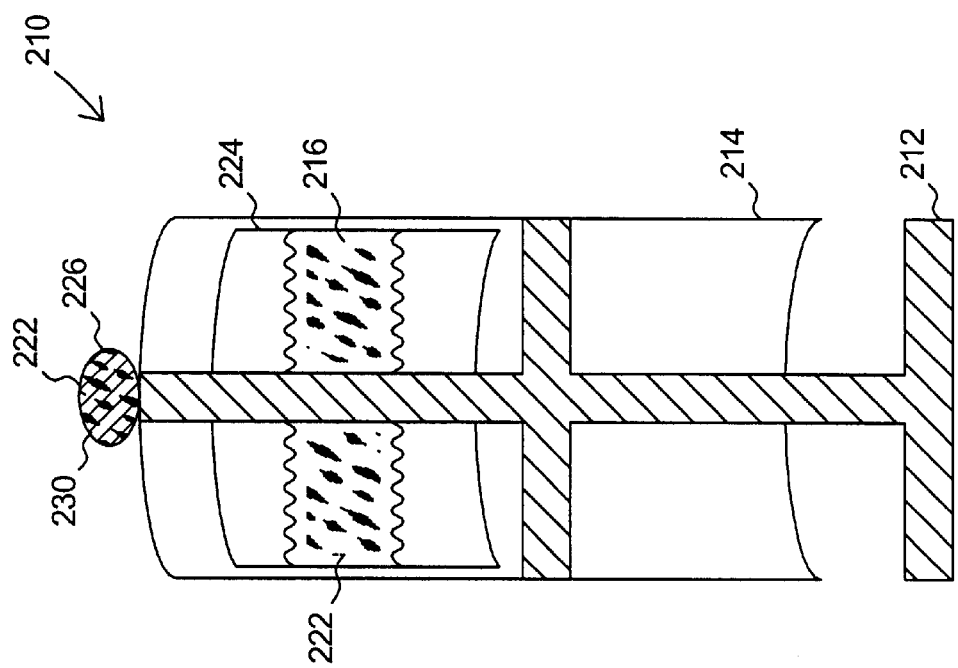

Referring also to FIGS. 4B–4C, the applicator 210 can be assembled and used in manners similar to those for assembling and using the applicators 10 and 110. To assemble the applicator 210, the cartridge 216 is inserted into the applicator tube 214. The cartridge 216 is preferably inserted into the tube 214 such that the top wall 224 of the cartridge 216 is disposed within the applicator tube 214. To use the applicator 210, the plunger 212 is pushed distally into the applicator tube 214 and the cartridge 216 such that the penetrable barriers 218, 220 are penetrated by the tip 226. The PCL material 222 combines with the catalyst 230 as the tip 226 passes between the barriers 218, 220. The plunger 212 is pushed until the tip 226 penetrates through the top wall 224 of the cartridge 216, exposing the combined PCL material 222 and catalyst 230. The compound of the PCL material 222 and the catalyst 230 is applied to a substrate by moving the tip 226 into close proximity and/or contact with the substrate. The used cartridge 216 may be removed and replaced by a fresh/new cartridge 216.

Figure 5C:
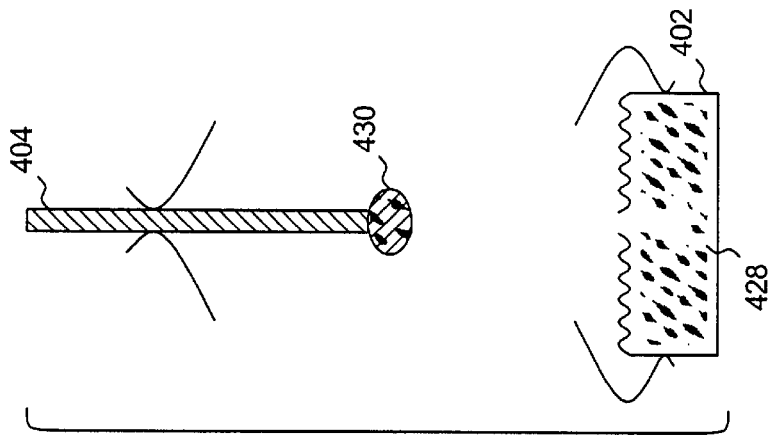
FIGS. 5A–5C are cross-sectional views of another applicator in three different positions during use.
Figure 5B:
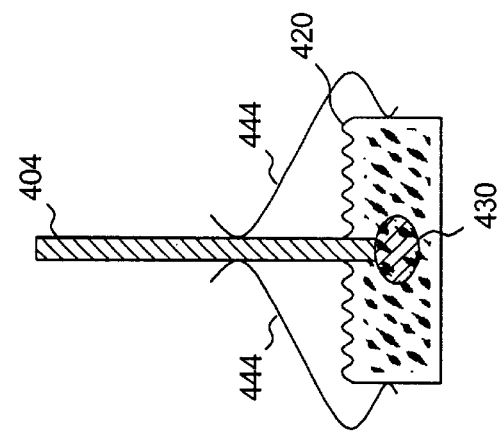
Figure 5A:
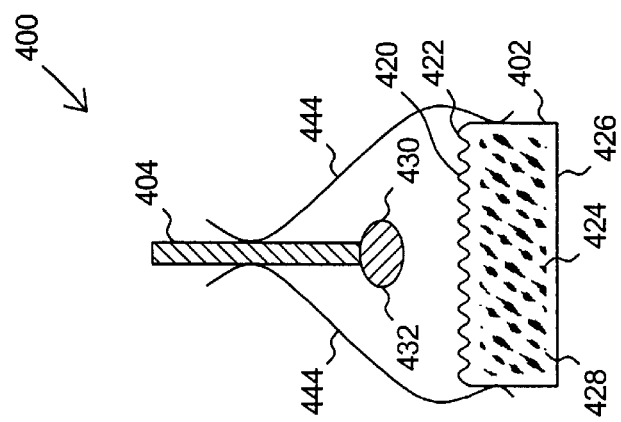

Referring to FIGS. 5A–5C, a push-pull applicator 400 includes a cartridge 402 and a plunger 404. The cartridge 402 includes a cup-shaped container 426 that is sealed by a penetrable barrier 420. The barrier 420 may be located at an end 422 of the container 426 or may be located inwardly from the end 422. As shown in FIG. 4A, a sealed chamber 424 is formed by the container 426 and the barrier 420. The chamber 424 holds a PCL material 428. A tip 430 of the plunger 404 is configured to receive and hold a catalyst 432 for combining with the PCL material 428.

The device 400 also includes a flexible attachment mechanism 444 configured to detachably connect the plunger 404 to the cartridge 402 so that the applicator tip 430 of the plunger 404 is located adjacent to the barrier 420, as shown in FIG. 4A. The attachment mechanism 444 may comprise, e.g., a cohesive paper (that adheres to itself under pressure, but preferably adheres to nothing else), or other similar material. The mechanism 444 may also comprise perforations to facilitate the detachment of the plunger 404 from the cartridge 402. The attachment mechanism 444 may also, or alternatively, be bonded weakly to the plunger 404 such that the plunger 306 can be separated from the attachment mechanism 444 by pulling the plunger 404 proximally (i.e., in a direction away from the cartridge 402).

The device 400 may be used to mix the catalyst 432 held by the applicator tip 430 with the PCL material 428 and to apply the resulting mixture to a substrate (not shown). To use the applicator 400, the plunger 404 is pushed such that applicator tip 430 penetrates the barrier 420, as shown in FIG. 5B. By penetrating barrier 420 with the applicator tip 430, the applicator tip 430 comes into contact with the PCL material 430, causing the material 430 to combine with (e.g., mix, absorb, adsorb, etc.) the catalyst 432 to form a compound.

The plunger 404, including the compound of the PCL material 428 and the catalyst 432, is removed from the cartridge 402 and the compound is applied to a desired substrate. The plunger 404 is pulled proximally in a direction away from cartridge 402 with enough force to separate the plunger 404 from the attachment mechanism 444 (e.g., by ripping, tearing, or breaking the attachment mechanism 444, or by overcoming a friction fit between the plunger 404 and the mechanism 444, etc.), as shown in FIG. 5C. The separated plunger 404 is moved into close proximity and/or contact with a desired substrate to apply the compound to the substrate.

Referring to FIGS. 6A–6B, an applicator 510 includes a plunger 512, an applicator tube 514, and a cartridge 516. The cartridge 516 includes a cartridge tube 526 that has an angled top 528. The cartridge 516 also comprises penetrable barriers 520 and 522. The barriers 520, 522 are attached to the tube 526 such that a chamber 528 is formed by the barriers 520, 522 and the tube 526 that contains a PCL material 530. The cartridge 516 also comprises an applicator tip 532. The applicator tip 532 is configured in a bottle cap or cup shape and covers a slanted top 534 of the tube 526. Applicator tips of other shapes are acceptable, however, such as a rounded tip 538 shown in FIG. 6C. The tip 532 is impregnated with a catalyst 536 and is configured to allow the PCL material 530 to permeate the tip 532 to form a compound 540 with the catalyst 536 and to allow the compound 540 to pass to the exterior of the tip 532. The plunger 512 has a slanted top that can direct more of the material 528, and more of the compound 540, to a desired portion of the tip 532 (or the tip 538 or a tip of another design). The device 510 may be used without the tube 514, e.g., if the cartridge 526 is configured to be pulled relative to the plunger 512 (e.g., by having flanges).

The device 510 can be used to mix the catalyst 536 that has been applied to applicator tip 532 with the PCL material 530 and to apply the resulting compound 540 to a substrate (not shown). The plunger 512 is pushed relative to the cartridge 516 such that the plunger 512 penetrates both of the barriers 520, 522 and forces the PCL material 530 into contact with the applicator tip 532. The material 530 combines (e.g., mixes) with the catalyst 536 to form the compound 540. The compound 540 passes through the tip 532 to the exterior surface of the tip 532. The resulting compound 540 is applied to a substrate by moving the tip 532 into close proximity/contact with the substrate.

Figure 7:
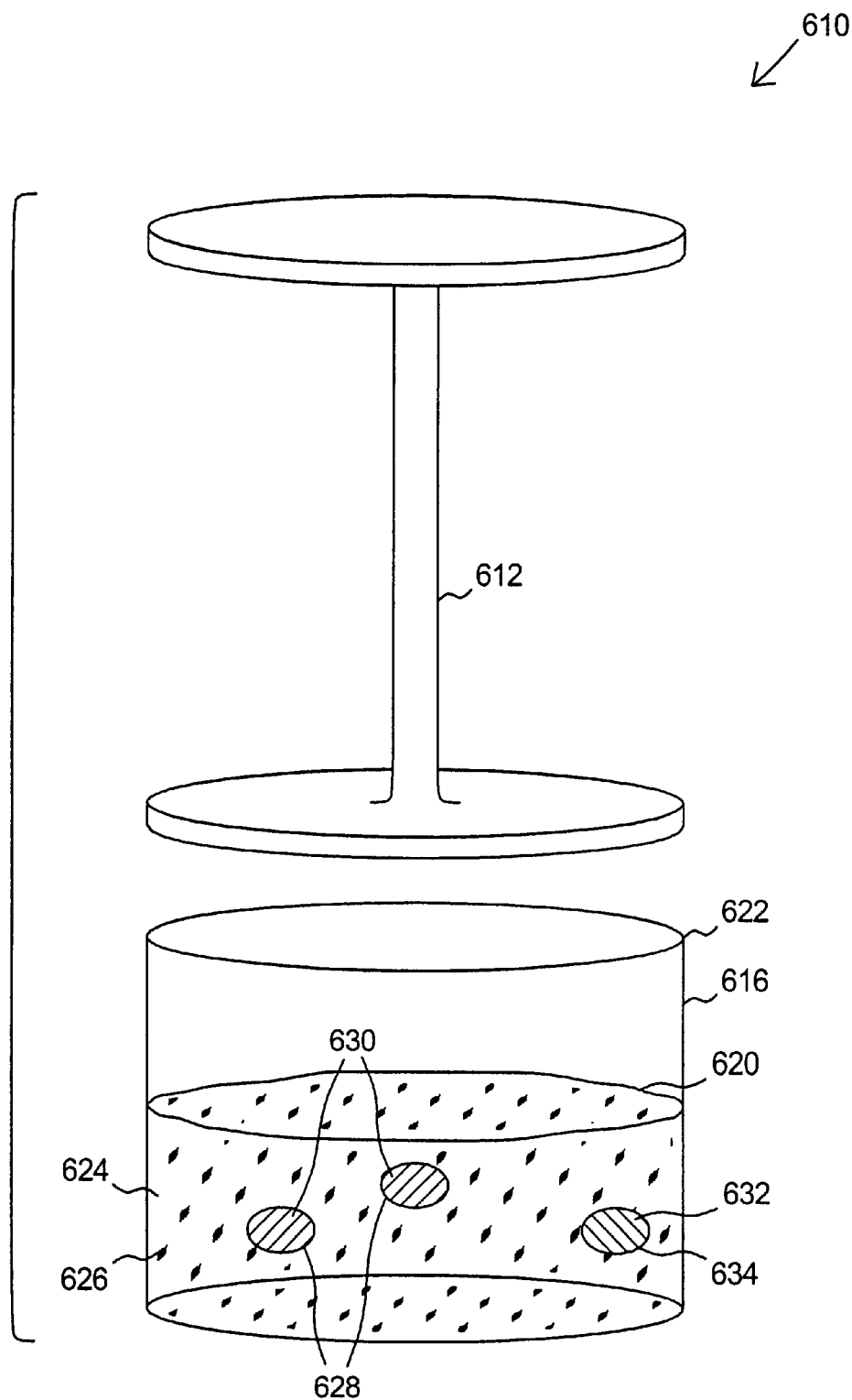
FIG. 7 is a perspective view of another applicator.

Referring to FIG. 7, an applicator 610 includes a plunger 612, and a cartridge 616. The cartridge 616 is a cup-shaped container that is sealed by a penetrable barrier 620. The barrier 620 may be located near an end 622 of the cartridge container 616, i.e., disposed at or inwardly from the end 622. A sealed chamber 624 is formed by the container 616 and the barrier 620 and holds a PCL material 626. The container 616 provides one or more holes 628 (although multiple holes 628 are shown) that are covered by penetrable barriers 630. The container 616 further includes an applicator tip 632 disposed over and covering each hole 628 and barrier 630 (only one tip 632 is shown in FIG. 7). Similar to other applicators, the tips 632 of the applicator 610 contain a catalyst 634 appropriate for the PCL material 626.

To use the device 610 to mix the catalyst 634 with the PCL material 626, the plunger 612 is depressed such that the plunger 612 forces the material 626 to break through the barriers 630 and be expelled through the holes 628. The material 626 expelled through the holes 628 contacts the corresponding applicator tips 632 and combines with the catalyst 634 to form a compound. The compound can be applied to a substrate by moving the cartridge into close proximity and/or contact with the substrate.

The device 610 may also comprise a hollow barrel or tube, e.g., similar to the applicator tube 14 (FIG. 1A), for receiving the cartridge 616. In this case, the cartridge 616 may be inserted into the tube to secure the cartridge 616 in the tube while the plunger 612 is depressed.

Figure 8:
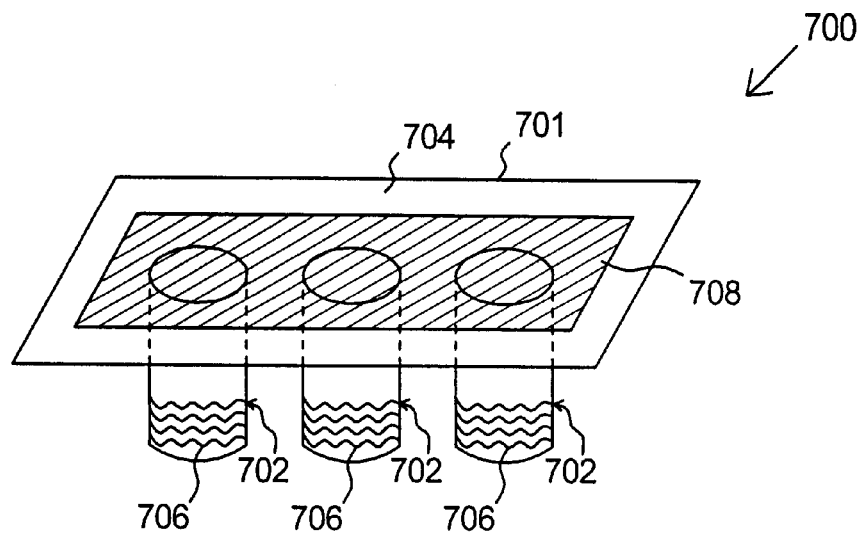
FIG. 8 is a perspective view of a package for holding multiple portions of a compound component.

Referring to FIG. 8, a package 700 for storing one or more PCL materials includes a base 701 that provides several, here three, cups 702 and that has a planar surface 704. Preferably, the base 701 is a single piece of molded plastic, e.g., a thermoformed piece of PET or HDPE, and possibly with a fluorination treatment post formation. Each of the cups 702 is configured to hold a PCL material 706, with each of the cups 702 potentially holding different PCL materials 706. The package 700 further includes a penetrable barrier 708 that is disposed on top of and adhered to the planar surface 704, and seals each of the cups 702. The barrier 708 helps retain the material 706 in the cups 702 absent the barrier 708 covering the cups 702 being penetrated. Multiple penetrable barriers may be provided for any, or each, of the cups 702 to provide for containing multiple, separated components. These components may contain all the components needed/desired to be combined, e.g., both a PCL material and a catalyst.

Figure 9:
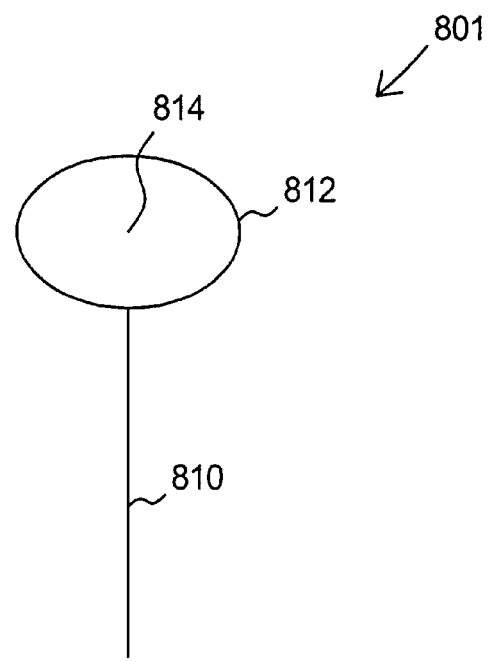
FIG. 9 is a side view of an applicator for use with the package shown in FIG. 8.

Referring also to FIG. 9, the package 700 may be placed together with at least one swab-type applicator 801 in a carton or other larger package (not shown). The applicator 801 includes a shaft or handle 810 and an applicator tip 812. The carton containing the package 700 and the applicator(s) 801 is provided to users (e.g., by being sold, e.g., at drugstores and supermarkets). The user can push the applicator tip 812 through the barrier 708 into one of the cups 702 to cause a catalyst 814 retained by the tip 812 to combine with the PCL material 706 (e.g., by being absorbed and/or adsorbed by the tip 812) to form a compound. If the cup 702 has multiple penetrable barriers, then each barrier may be penetrated and corresponding components contained between barriers or a barrier and the cup wall, combined on/in the applicator tip 812. The tip 812 may, or may not, be devoid of a component if the multiple barriers enclose all desired components. The tip 812 can be removed from the cup 702 moved into close proximity and/or contact with a desired portion of a desired substrate such that the compound will be applied to the desired substrate portion.

Figure 10:
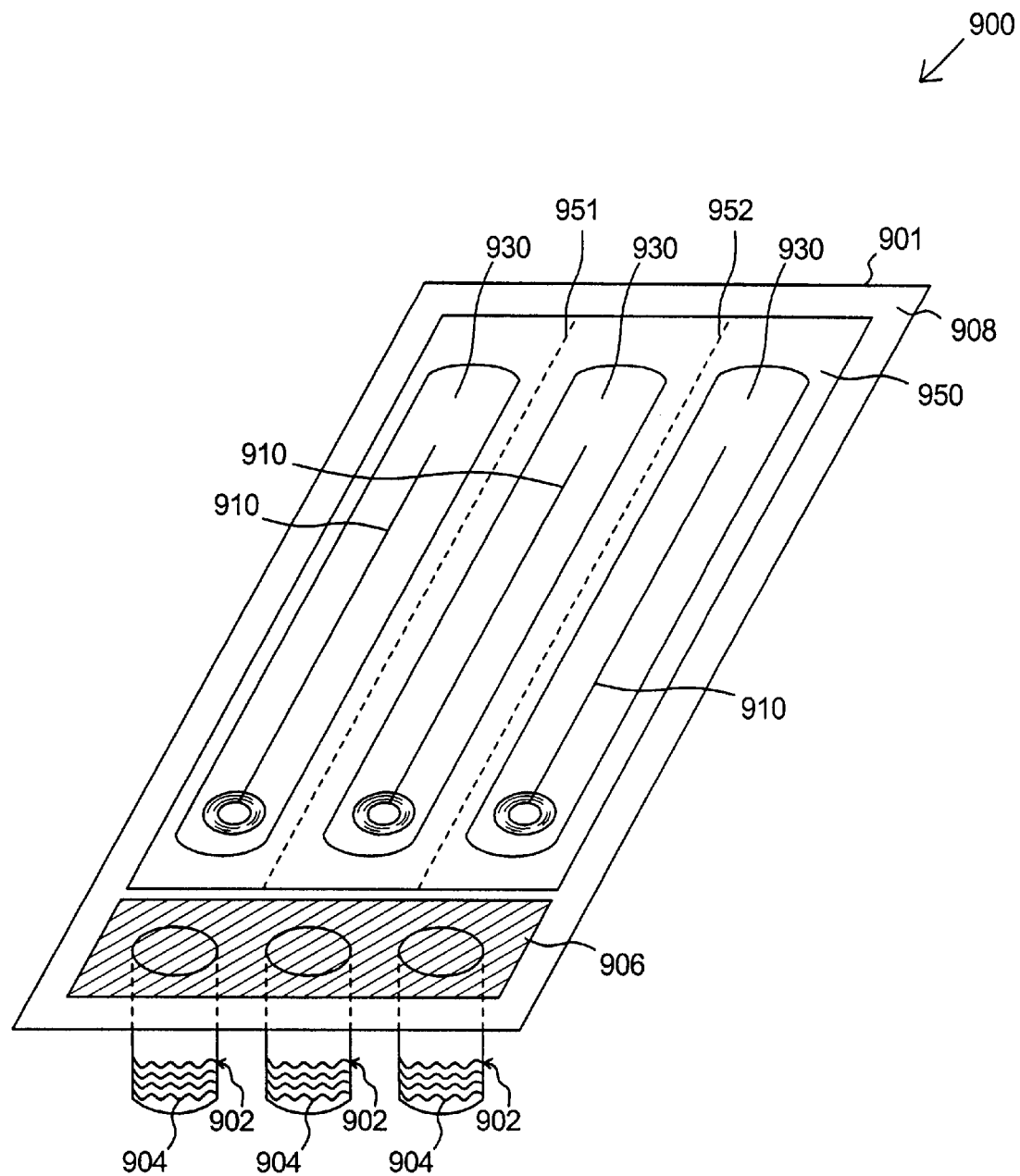
FIG. 10 is a perspective view of a package for holding multiple portions of a compound component and multiple corresponding applicators for use with the portions of the compound component.

Referring to FIG. 10, a package 900 for storing PCL material and applicators includes a base 901 that provides several, here three, cups 902. Preferably, the material 901 is a molded plastic, e.g., a thermoformed piece of PET or HDPE, and possibly with a fluorination treatment post formation. Each of the cups 902 holds a PCL material 904. The package 900 further includes a penetrable barrier 906 that is disposed on top of and adhered to a planar surface 908 of the base 901 so that each of the cups 902 is sealed by a portion of the penetrable barrier 906. The barrier 906 helps retain the material 904 in the cups 902 absent the barrier 906 covering the cups 902 being penetrated. As with the cups 702 of the package 700 shown in FIG. 8, the cups 902 of the package 900 may include multiple penetrable barriers retaining multiple components to be combined.

In addition to providing the cups 902, the base 901 provides several, here three, channels or recesses 930 corresponding to the cups 902. An applicator 910, similar to the applicator 801 shown in FIG. 9, is disposed in each one of the channels or recesses 910. The package 900 further includes a cover 950 formed of a thin layer of material, e.g., paper, that is placed over the channels 910 and adhered to the base 901 and/or the barrier 906. The cover 950 retains the applicators 910 in the corresponding channels 930 absent rupturing or removal of the cover 950. Preferably, the cover 950 is made of paper. The cover 950 may be perforated along lines 951, 952 to facilitate removal of portions of the cover 950 to gain access to desired applicators 910. A portion of the cover 950 may be removed or ruptured and the corresponding applicator 910 removed from its recess 910. The applicator 910, and in particular its tip containing an appropriate catalyst, can be inserted through the barrier 906 into a desired one of the cups 902. The catalyst and the PCL material 904 will combine, and the combination may be applied to a desired substrate. The applicators' tips may, or may not, be devoid of a compound component if the cups 902 include multiple compound components. The components on the applicators 910 may correspond to the components in the cups 902 (e.g., with different components in the different cups 902 and/or on the different applicators 910). Also, the cover 950 may extend over and cover the cups 902, e.g., to help the barrier 906, as well as the applicators 910, clean (e.g., sterile) until use.

Figure 11:
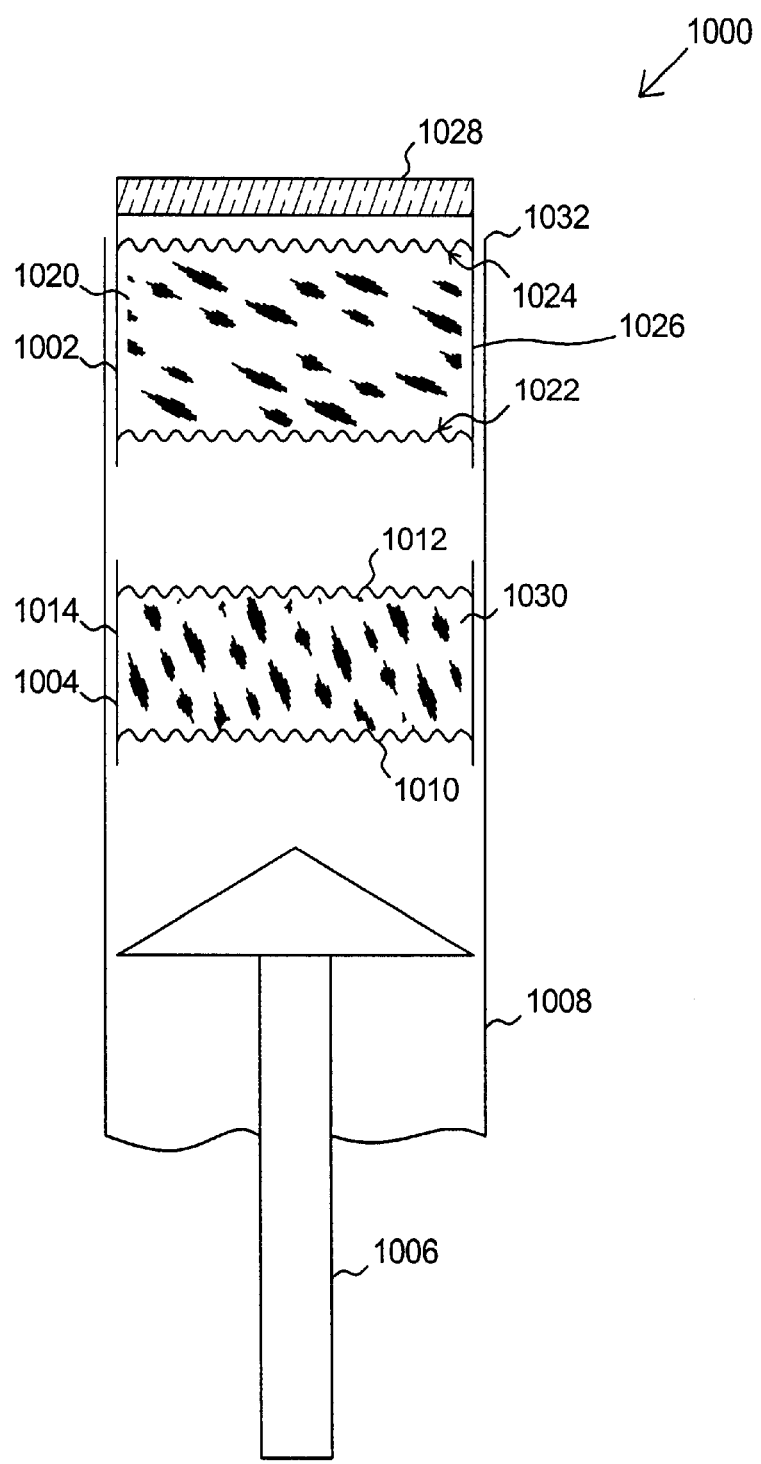
FIGS. 11–12 are cross-sectional views other applicators.

Referring to FIG. 11, a multi-cartridge applicator 1000 includes a distal cartridge 1002, a proximal cartridge 1004, a hollow barrel or tube 1008, and a plunger 1006. The distal cartridge 1002 is similar to the cartridge 16 shown in FIG. 1A although a tip 1028 of the cartridge 1002 is different from the tip 24 of the cartridge 16. The applicator tip 1028 does not include a catalyst, although the tip 1028 may be made of the same material and otherwise configured like the tip 24. Alternatively, the tip 1028 may include a catalyst, a PCL material, or any other desired compound component. The distal cartridge 1002 holds a PCL material 1020 between penetrable barriers 1022, 1024 and a tube 1026. The proximal cartridge 1004 is similar to the cartridge 216 shown in FIG. 3A, although penetrable barriers 1010, 1012 and a tube 1014 of the cartridge 1004 contain a catalyst 1030 instead of PCL material as contained by the cartridge 216. Alternatively, the cartridge 1002 can hold the catalyst and the cartridge 1004 can hold the PCL material.

The device 1000 can be used to mix the catalyst 1030 and the PCL material 1020 and to apply the resulting compound to a desired substrate. The cartridges 1004, 1002 are securely inserted into the hollow barrel 1008 so that the applicator tip 1028 extends beyond a distal end 1032 of the hollow barrel 1008. The plunger 1006 is depressed such that the plunger 1006 penetrates both of the barriers 1010, 1012 of the proximal cartridge 1004 and both of the barriers 1022, 1024 of the distal cartridge 1002. As the plunger proceeds distally, the catalyst 1030 will combine with the PCL material 1020 to form a compound. By further depressing plunger 1006, the compound can be absorbed or adsorbed by the applicator tip 1028. The compound exits, or is disposed in, the tip 1028 and can be applied to a desired substrate by moving the tip 1028 close to and/or into contact with the substrate (e.g., if the compound is not available on a surface of the tip 1028, then contacting the tip 1028 with the substrate can bring the compound into contact with the substrate).

The cartridges 1002, 1004 can be removed from the tube 1008 so that the tube 1008 and the plunger 1006 can be used again with a new cartridges. In this manner, the device 1000 may be reusable, although the device 1000 may also be a single use device.

Variations of the device 1000 are also possible. For example, the distal cartridge 1002 may not include the applicator tip 1028, and the plunger 1006 can be replaced with a plunger similar to the plunger 212 shown in FIG. 4A, with a tip of the plunger preferably not containing a catalyst (although it could contain a catalyst or other compound component) as that will be supplied in one of the cartridges 1002, 1004. In this case, the tip 1028 is preferably not used, but may be replaced by a further penetrable barrier. Further, the tip 1028 may be replaced with a substantially impenetrable wall and the plunger 1006 replaced with a plunger similar to the plunger 212, or a swab-type plunger (e.g., the applicator 801 shown in FIG. 9), used in a push-pull fashion to combine the materials 1020, 1030 and to remove the plunger for application of the compound to a substrate. In this case, the barrier 1024 is preferably not used.

Figure 12:
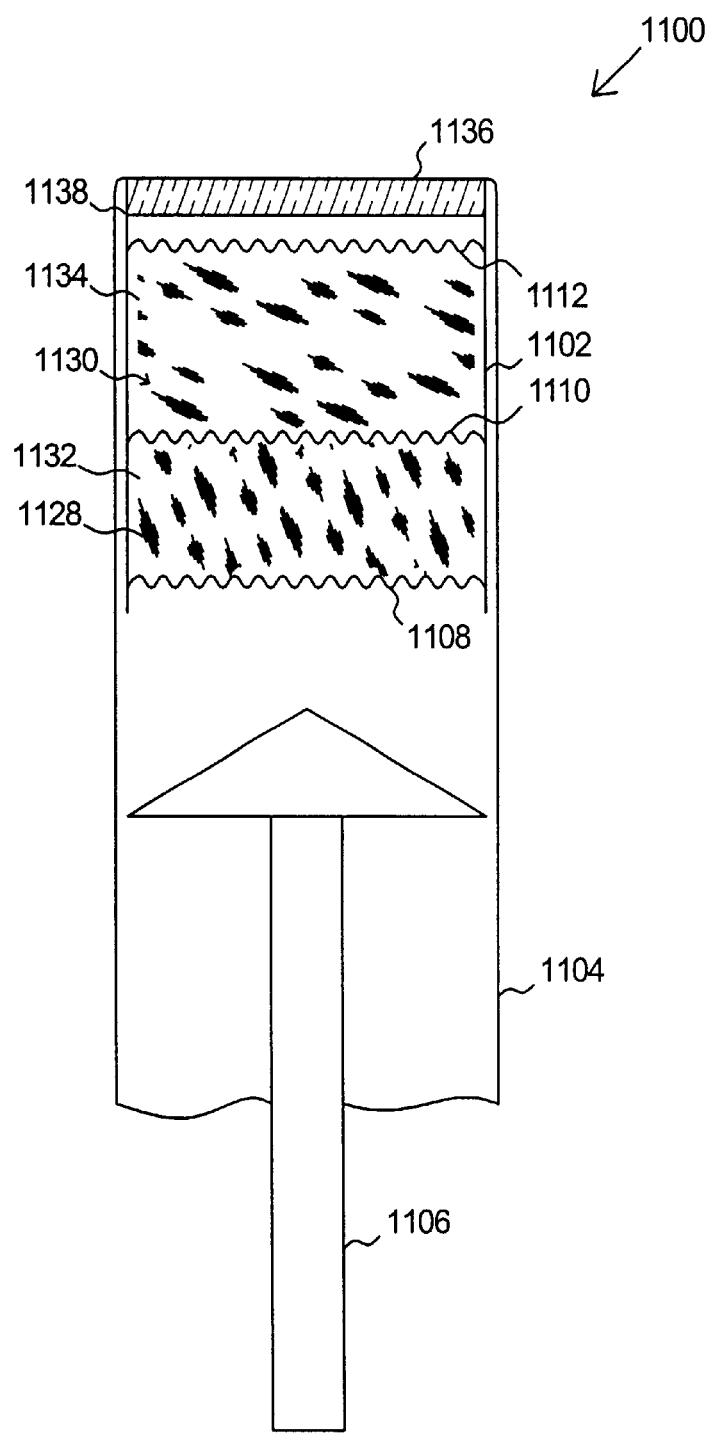

Referring to FIG. 12, another multi-cartridge applicator 1100 includes a cartridge 1102, a hollow barrel or tube 1104, and a plunger 1106. The cartridge 1102 is similar to the cartridge 16 shown in FIG. 1A, although the cartridge 1102 includes a proximal penetrable barrier 1108, an intermediate penetrable barrier 1110, and a distal penetrable barrier 1112. The barriers 1108, 1110, 1112 are attached to an inner wall of a tube 1126 to provide chambers 1128, 1130 that contain a PCL material 1132 and a catalyst 1134 (or vice versa), respectively. The cartridge 1102 also includes an applicator tip 1136 similar to the tip 1028 shown in FIG. 11.

The device 1100 can be used to mix the catalyst 1134 and the PCL material 1132 and to apply the resulting compound to a desired substrate. The cartridge 1102 is inserted securely into the tube 1104 so that applicator tip 1136 extends beyond a distal end 1138 of the tube 1104. The plunger 1106 is depressed such that the plunger 1106 penetrates all of the barriers 1108, 1110, 1112 of the cartridge 1102. This action causes the catalyst 1134 to mix with the PCL material 1132 to form a compound. By further depressing plunger 1106, the compound can be absorbed or adsorbed by the applicator tip 1136 and become available for application to a substrate. The compound exits, or is disposed in, the tip 1136 and can be applied to a desired substrate by moving the tip 1136 close to and/or into contact with the substrate (e.g., if the compound is not available on a surface of the tip 1136, then contacting the tip 1136 with the substrate can bring the compound into contact with the substrate).

Variations of the device 1100 are also possible. For example, the cartridge 1102 may not include the applicator tip 1136 and the plunger 1106 may be replaced with a plunger similar to the plunger 212 shown in FIG. 4A, with a tip of the plunger preferably not containing a catalyst (although it could contain a catalyst or other compound component) as that will be supplied in the cartridges 1102. In this case, the tip 1136 is preferably not used, but may be replaced by a further penetrable barrier. Further, the tip 1136 may be replaced with a substantially impenetrable wall and the plunger 1106 replaced with a plunger similar to the plunger 212, or a swab-type plunger (e.g., the applicator 801 shown in FIG. 9), used in a push-pull fashion to combine the materials 1132, 1134 and to remove the plunger for application of the compound to a substrate. In this case, the barrier 1112 is preferably not used.

The tubes, barrels, and containers described herein can be constructed from a wide variety of materials, but preferably are constructed from a plastic material. For medical applications, the materials are preferably of surgical grade.

Also, as shown in many of the figures, many of the materials may be transparent. Further, the tubes and barrels are preferably cylindrical in shape, but other shapes are contemplated.

Other embodiments are within the scope and spirit of the appended claims. For example, the applicator 10 configured as a single-use applicator may have not have a separate cartridge, and may have only one penetrable barrier that separates the PCL material (or other desired material) from the tip 24. Further, an applicator similar to the applicator 210 shown in FIG. 4A can be used where the tube 214 is replaced with a tube having a closed distal end. In this case, the plunger 212 can be pushed such that the tip 226 penetrates the barrier 218, and pulled to remove the plunger 212 and expose the tip 226 with the compound of the PCL material 222 and the catalyst 230 for application to a desired substrate. If desired, the barrier 216 may not be used, especially if the barrier 224 is replaced with a substantially impenetrable wall. Further, where penetrable barriers/membranes are used, multiple penetrable barrier may be used, and if so, the barriers may or may not be separated (e.g., displaced from each other with, e.g., air between them); for example, the arrangements of the barriers 1012, 1022 in FIG. 11 and the barrier 1120 in FIG. 12 may be interchangeable. Also, the term sealing as used herein does not require that the seal be disposed at a particular location (e.g., the seal can be provided at various locations, e.g., in the tube 18 shown in FIG. 1A, or any other cavity, passageway, receptacle, etc.).

Also for example, although the invention has been noted to be useful in medical applications such as wound closure, the invention is useful in numerous other applications, a non-exhaustive list of which is provided below. The invention can find use in applications that involve, e.g., addition of dyes or colorants to a product, addition of a performance-enhancing/altering chemical to a product, combining multiple components such as sealants and caulks or adhesives or fillers, and combining of multiple components to initiate a desired reaction. For each application, appropriate components (e.g., PCL material and catalyst, epoxy elements, etc.), and an appropriate embodiment of the invention (including design (e.g., for number of components) and materials appropriate for the components) are selected and used.

Cartridge-based delivery systems may be used for combining any combination of pharmaceutical products for which data supporting safety and efficacy is available. These delivery systems can accommodate the combining at point of use and topical, oral, or internal application of any combination of antibiotics, medications, antibacterial agents, anti-inflammatory products, local anesthetics, antiseptics, painkillers, growth stimulators, haemostatic agents, anti-adhesion agents, moisturizers, and wound closure adhesives, as well as others.

At least some embodiments of the invention can support the implantation of medical products that combine at the point of use, or whose performance can be enhanced by the addition of some added material. Some examples of such applications are implantable products (including hemostats, surgical mesh products, bulking agents, dressings, and transdermal patches), reagent testing, dental applications, veterinary applications, and consumer uses.

Hemostat-related applications can include hemostats, tissue sealants, and adhesion prevention products. For such applications, embodiments of the invention can accommodate the passage of a pre-configured or malleable hemostat through a cartridge filled with a second component, such as Thrombin, and can provide a method of applying the hemostat to the point of use. Potential applications are in the cardiovascular field as well as other surgical venues for controlling bleeding.

Surgical mesh products are used in numerous applications for surgical repair. For example, such products find use for abdominal wall repair, hernia repair, etc. that can be enhanced with the addition of various drug types via the same system as the hemostat.

Bulking agents are designed to essentially take up space to support internal anatomical structures. One example of a bulking agent application is radical prostetectomy, where a bulking agent may be injected into a gap created by the removal of the prostate in order to support the remaining internal structures. While these products are in development, they may resemble foam that expands to fill the space vacated by the removed organ. These products may be in the form of multiple parts that are separated until use.

Dressings are primarily topically-applied bandages that with the aid of the invention could be passed through medicine-containing cartridges at the point of application to a wound or treatment area. This wetted applique would be covered by a secondary bandage, or adhesive.

Transdermal patches can be passed through a cartridge containing a carefully measured amount of a product. Thus, embodiments of the invention could support "mix at point of use" transdermal patches using a common sized patch with cartridges filled by volume. Such embodiments could provide unit dose transdermal delivery as opposed to pre-made patches. Such embodiments could provide for combining pharmaceutical product types for a transdermal application as needed for an individual patient.

Reagent testing applications can be pursued utilizing a reagent chemical supplied in a cartridge along with a swab in a common tube. The swab is removed, a sample taken as needed to support the test, and a penetrable membrane breached to combine the sample and the reagent. The cartridge is preferably made of a transparent material such that the reaction (color change, etc.) may be viewed thus determining a test result. Actual reagent applications potentially include, but are not limited to, water sampling tests, oral fluid tests, influenza tests, adjuncts to PAP test methodologies, and forensic crime-scene tests. Oral fluid (saliva based) tests, e.g., for drug use/abuse, could employ embodiments of the invention such as various embodiments with plungers to combine saliva samples with appropriate reagents for determining the presence of drugs and/or alcohol. Influenza testing could use embodiments of the invention to efficiently and effectively combine a potential influenza sample with an appropriate reagent.

The dental industry uses a broad array of products that combine components at the point of use. For example, embodiments of the invention could be used with etching primers, bonding agents, colorants, tooth sealants, crack repair products, and fillers.

Veterinary applications for embodiments of the invention could include wound closure and drug delivery. Wound closure applications for animals include cat claw removal, minor lacerations and abrasions, surgical incisions including oral surgeries, and dew claw removal.

Consumer use applications for embodiments of the invention are essentially boundless. Exemplary applications include, but are not limited to, automobile and/or boat repair, cosmetics, home drug testing, at-home dental care, plumbing products, furniture repair, electronics, and food products. Automobile/boat repair applications can include finishing products, scratch repair products, upholstery repair products, bonding agents, and fiberglass repair. Cosmetics applications can include combining (e.g., mixing) colors (e.g., of makeup), eyeliner, lipstick, lip balm, hair dyes, skin treatments, and hair streaking, tinting, and/or highlighting chemicals. Home drug testing applications include oral fluid reagent testing for substances such as alcohol or narcotics. At-home dental care applications include toothbrushes, water jet cleaning apparatus, or other apparatus that deliver, e.g., combinations of water, toothpaste, medication, sealant, flavor enhancement, breath freshener, etc. Plumbing product applications include porcelain repair products, caulks, sealants, and adhesives. Furniture repair applications include finishing products, varnishes, scratch repair and filler products. Electronics applications include cleaners, e.g., for keyboards or computer screens. Food product applications include cake decorating (e.g., forcing cake icing through a cartridge containing coloring, and out of a tip), salad dressings, and snack foods. The above lists provide non-exhaustive examples of applications for the listed categories.

What is claimed is:

1. A device for use in combining components to form a compound and for applying the compound to a substrate, the device comprising:
   a first housing having a first-housing receptacle with a proximal end;
   a plunger including a proximal end and a distal end, the distal end being disposed in the proximal end of the first-housing receptacle;
   at least one penetrable barrier sealing the receptacle; and
   a first component of the compound disposed in the first-housing receptacle;
   wherein one of the first housing and the plunger includes an applicator tip retaining a second component of the compound and being separated from the first component by the at least one penetrable barrier.

2. The device of claim 1 further comprising a second housing, that provides a second-housing receptacle, and a cartridge comprising a cartridge housing that provides a cartridge-housing receptacle and that is configured to be securely and releasably received by the first-housing receptacle.

3. The device of claim 2 wherein the at least one penetrable barrier includes at least two penetrable barriers sealing the cartridge-housing receptacle and wherein the first component is disposed between the at least two penetrable barriers.

4. The device of claim 1 wherein the at least one penetrable barrier includes at least two penetrable barriers sealing the first-housing receptacle and wherein the first component is disposed between the at least two penetrable barriers.

5. The device of claim 4 wherein the applicator tip is coupled to the first housing at a distal end of, and in fluid communication with, the first-housing receptacle.

6. The device of claim 1 wherein the applicator tip is coupled to the distal end of the plunger, and wherein the first housing includes a back wall providing a closed distal end of the first-housing receptacle, and wherein the at least one penetrable barrier is disposed between the back wall and the distal end of the plunger.

7. The device of claim 1 wherein the first component of the compound is disposed in the receptacle between a distal end of the receptacle and the at least one penetrable barrier.

8. The device of claim 1 wherein a distal end of the plunger is configured to at least one of facilitate penetration of the at least one penetrable barrier by the distal end of the plunger, and direct the first compound in a desired direction.

9. A device for use in combining components of a compound for application to a substrate, the device comprising:
   a body providing a body cavity;
   a first penetrable membrane sealing the body cavity;
   a second penetrable membrane sealing the body cavity and being disposed distally in the body cavity relative to the first penetrable membrane;
   a first compound component disposed between the first and second penetrable membranes; and
   a second compound component disposed in the body cavity distally from the second penetrable membrane.

10. The device of claim 9 wherein the body comprises a base, that provides a base cavity, and a cartridge comprising a cartridge housing that provides a cartridge-housing cavity and that is configured to be securely and removably received by the base cavity, the base cavity and the cartridge-housing cavity providing the body cavity while the cartridge housing is received by the base cavity.

11. The device of claim 10 wherein the first and second membranes and the first and second compound components are disposed within the cartridge-housing cavity.

12. The device of claim 9 wherein the body includes a porous tip disposed and covering a distal end of the body cavity.

13. The device of claim 12 wherein the tip includes a third compound component.

14. The device of claim 9 further comprising a plunger having a distal end configured to be extendable into the body cavity and to penetrate the first and second membranes.

15. The device of claim 14 wherein the plunger includes a tip configured to receive the first and second components.

16. The device of claim 9 further comprising a third penetrable membrane sealing the body cavity and disposed distally from the second penetrable membrane, wherein the second compound component is disposed between the second and third penetrable membranes.

17. The device of claim 16 further comprising a fourth penetrable membrane sealing the body cavity and disposed distally from the first penetrable membrane and proximally from the second penetrable membrane, wherein the first compound component is disposed between the first and fourth penetrable membranes.

18. An apparatus for use in combining compound components to form a compound, and for use in applying the compound to a substrate, the apparatus comprising:
   a plurality of containers each having an open, proximal end and a closed, distal end;
   at least one first penetrable membrane sealing the open, proximal end of each of the plurality of containers;
   a second penetrable membrane sealing a particular one of the containers between the corresponding open, proximal end and the corresponding closed, distal end;
   a first compound component disposed in the particular one of the containers between the first penetrable membrane and the second penetrable membrane; and
   a second compound component disposed in the particular one of the containers between the second penetrable membrane and the corresponding closed, distal end.

19. An apparatus for use in combining compound components to form a compound, and for use in applying the compound to a substrate, the apparatus comprising:
   a plurality of first containers each having a first open, proximal end and a first closed, distal end;

a plurality of second containers each coupled and corresponding to a respective first container, each of the second containers having a second open, proximal end and a second closed, distal end;

at least one penetrable membrane sealing the first open, proximal ends of the plurality of first containers;

at least one cover disposed over the first open, proximal ends of the plurality of second containers;

a plurality of devices disposed in the plurality of second containers and configured to hold the compound for application to the substrate;

a first compound component disposed in at least a particular one of the first containers between the at least one penetrable membrane and the first closed, distal end of the particular first container; and a second compound component disposed in at least one of the at least a particular one of the first containers and at least one of the second containers.

20. The apparatus of claim 19 wherein at least a particular one of the devices disposed in the second containers has a tip having the second component.

21. The apparatus of claim 20 wherein the at least a particular one of the devices is disposed adjacent to the at least a particular one of the first containers.

22. A cartridge for use with a housing that provides a receptacle, the cartridge comprising:

a body configured to be removably and securely received by the housing receptacle, the body providing a cavity extending from a proximal exterior surface of the body;

a first penetrable barrier sealing the cavity; and a first compound component disposed distally in the cavity from the penetrable barrier.

23. The cartridge of claim 22 further comprising a second penetrable barrier sealing the cavity and being displaced distally from the first penetrable barrier, and wherein the compound component is disposed between the first and second barriers.

24. The cartridge of claim 23 further comprising:

a third penetrable barrier sealing the cavity and being displaced distally from the second penetrable barrier; and a second compound component disposed in the cavity between the second and third compound components.

25. The cartridge of claim 24 further comprising a fourth penetrable membrane sealing the cavity and disposed distally from the second barrier and proximally from the third barrier, wherein the second compound component is disposed between the third and fourth compound components.

26. The cartridge of claim 25 wherein the body comprises a substantially impenetrable wall covering a distal end of the cavity.

27. The cartridge of claim 22 further comprising a tip coupled to the body and covering a distal end of the cavity, the tip being configured to receive the first compound component.

28. The cartridge of claim 27 wherein the tip includes a second compound component, and is configured to retain the compound, formed by the first and second compound components when the tip receives the first compound component, for application to a substrate.

29. A device for use in combining components to form a compound and for use in applying the compound to a substrate, the device comprising:

a housing providing a receptacle at least partially through the housing and a hole through a wall of receptacle;

a plunger including a proximal end and a distal end, at least the distal end being configured to be extendable into a proximal end of the receptacle in the housing;

a penetrable barrier sealing the receptacle proximally relative to the hole provided by the housing;

a frangible membrane sealing the hole provided by the housing;

a first component of a compound disposed in the receptacle distally from the penetrable barrier; and a porous member coupled to the housing and disposed over the hole and the frangible membrane, the porous member retaining a second component of the compound and configured to receive the first component of the compound.

* * * * *